(12) United States Patent
Braunstein et al.

(10) Patent No.: US 12,373,253 B2
(45) Date of Patent: Jul. 29, 2025

(54) DISTRIBUTED MEDICAL SOFTWARE PLATFORM

(71) Applicant: GE Precision Healthcare LLC, Milwaukee, WI (US)

(72) Inventors: Michael Braunstein, Mequon, WI (US); Aparna Nittala, Waukesha, WI (US); Fausto Espinal, Delafield, WI (US); Roshni Bhagalia, Wales, WI (US); Murali Kumaran Kariathungal, Hoffman Estates, IL (US)

(73) Assignee: GE Precision Healthcare LLC, Waukesha, WI (US)

( * ) Notice: Subject to any disclaimer, the term of this patent is extended or adjusted under 35 U.S.C. 154(b) by 952 days.

(21) Appl. No.: 17/451,747

(22) Filed: Oct. 21, 2021

(65) Prior Publication Data

US 2022/0164230 A1 May 26, 2022

Related U.S. Application Data

(60) Provisional application No. 63/116,506, filed on Nov. 20, 2020.

(51) Int. Cl.
*G06F 9/50* (2006.01)
*G06F 8/71* (2018.01)
*G16H 30/20* (2018.01)

(52) U.S. Cl.
CPC .............. *G06F 9/5005* (2013.01); *G06F 8/71* (2013.01); *G06F 9/50* (2013.01); *G06F 9/5027* (2013.01);
(Continued)

(58) Field of Classification Search
None
See application file for complete search history.

(56) References Cited

U.S. PATENT DOCUMENTS 10,437,647 B2 10/2019 Tseng et al.
10,587,463 B2 3/2020 Easterling et al.
(Continued)

FOREIGN PATENT DOCUMENTS

WO 2011/143568 A2 11/2011

OTHER PUBLICATIONS

Netto et al., "State Machine Replication in Containers Managed by Kubernetes", Dec. 24, 2016, Elsevier, Journal of Systems Architecture 73, pp. 53-59. (Year: 2016).*

(Continued)

*Primary Examiner* — Qing Yuan Wu
(74) *Attorney, Agent, or Firm* — Amin, Turocy & Watson, LLP

(57) ABSTRACT

Intelligent, distributed medical software management (e.g., using a computerized tool) is enabled. A system can comprise a processor, and a memory that stores executable instructions that, when executed by the processor, facilitate performance of operations, comprising determining requirement information representative of one or more requirements of a medical application of a group of medical applications, wherein the medical application is associated with a medical device, based on the requirement information, allocating elements of a cluster employable to host and run the medical application in a medical application container, wherein the elements of the cluster are determined to satisfy the requirement information, and in response to allocating the elements of the cluster, hosting the medical application in the medical application container, wherein hosting the medical application comprises communicatively coupling the medical application to the medical device.

20 Claims, 14 Drawing Sheets

(52) U.S. Cl.
CPC .......... *G06F 9/5077* (2013.01); *G06F 9/5083* (2013.01); *G16H 30/20* (2018.01)

(56) References Cited

U.S. PATENT DOCUMENTS

| | | | |
|---|---|---|---|
| 2014/0137179 A1 | 5/2014 | Christodorescu et al. | |
| 2018/0109625 A1 | 4/2018 | Jayaraman et al. | |
| 2020/0042359 A1* | 2/2020 | Zhang | G06F 9/5055 |
| 2020/0341786 A1* | 10/2020 | Soryal | G06F 9/5077 |
| 2021/0279111 A1* | 9/2021 | Ranjan | G06F 9/455 |
| 2022/0270753 A1* | 8/2022 | Hsu | A61B 5/7221 |

OTHER PUBLICATIONS

International Search Report and Written Opinion received for PCT Application Serial No. PCT/US2021/057118 dated Feb. 22, 2022, 13 pages.

International Preliminary Report on Patentability received for PCT Application Serial No. PCT/US2021/057118 dated May 16, 2023, 8 pages.

Braunstein, "EHL Next Generation Architecture," EHL Next Generation Architecture—Edison Healthlink—Developer Cloud, Nov. 13, 2020, https://devcloud.swcoe.ge.com/devspace/pages/viewpage. action?spaceKey=YDAZL&title=EHL +Next+Generation+ Architecture.

* cited by examiner

DISTRIBUTED MEDICAL SOFTWARE PLATFORM

CROSS-REFERENCE TO RELATED APPLICATIONS

This application claims the benefit of and priority to U.S. Provisional Application No. 63/116,506, filed Nov. 20, 2020, entitled "SYSTEMS, APPARATUSES, AND METHODS FOR HYBRID AND CLUSTERED CLINICAL SYSTEMS." The entirety of the aforementioned application is hereby incorporated herein by reference.

TECHNICAL FIELD

The disclosed subject matter relates to distributed medical software platforms and, more particularly, to scalable medical software platforms leveraging clustered architectures.

BACKGROUND

Healthcare facilities utilize a variety of medical devices. Modern medical devices increasingly leverage software and transmit data to other medical devices and systems in healthcare facilities. In general, medical software applications provide care and diagnostic information to assist clinicians in patient healthcare. Most healthcare institutions have many medical applications that are used in a variety of situations and purposes. Every medical application has its own set of compute requirements in order to meet expected clinical performance requirements.

Existing facilities rely on a patchwork of medical software and systems, and due to a variety of medical constraints, such as regulatory verification and validation requirements for medical technology, integration and management of such medical software and systems is increasingly complex, costly, and inefficient. Additionally, due to the entanglement of the patchwork of medical software and systems, hardware and/or software failures can cascade throughout a healthcare facility, thus jeopardizing its patients.

The above-described background relating to distributed medical software platforms is merely intended to provide a contextual overview of some current issues and is not intended to be exhaustive. Other contextual information may become further apparent upon review of the following detailed description.

DETAILED DESCRIPTION

Figure 1:
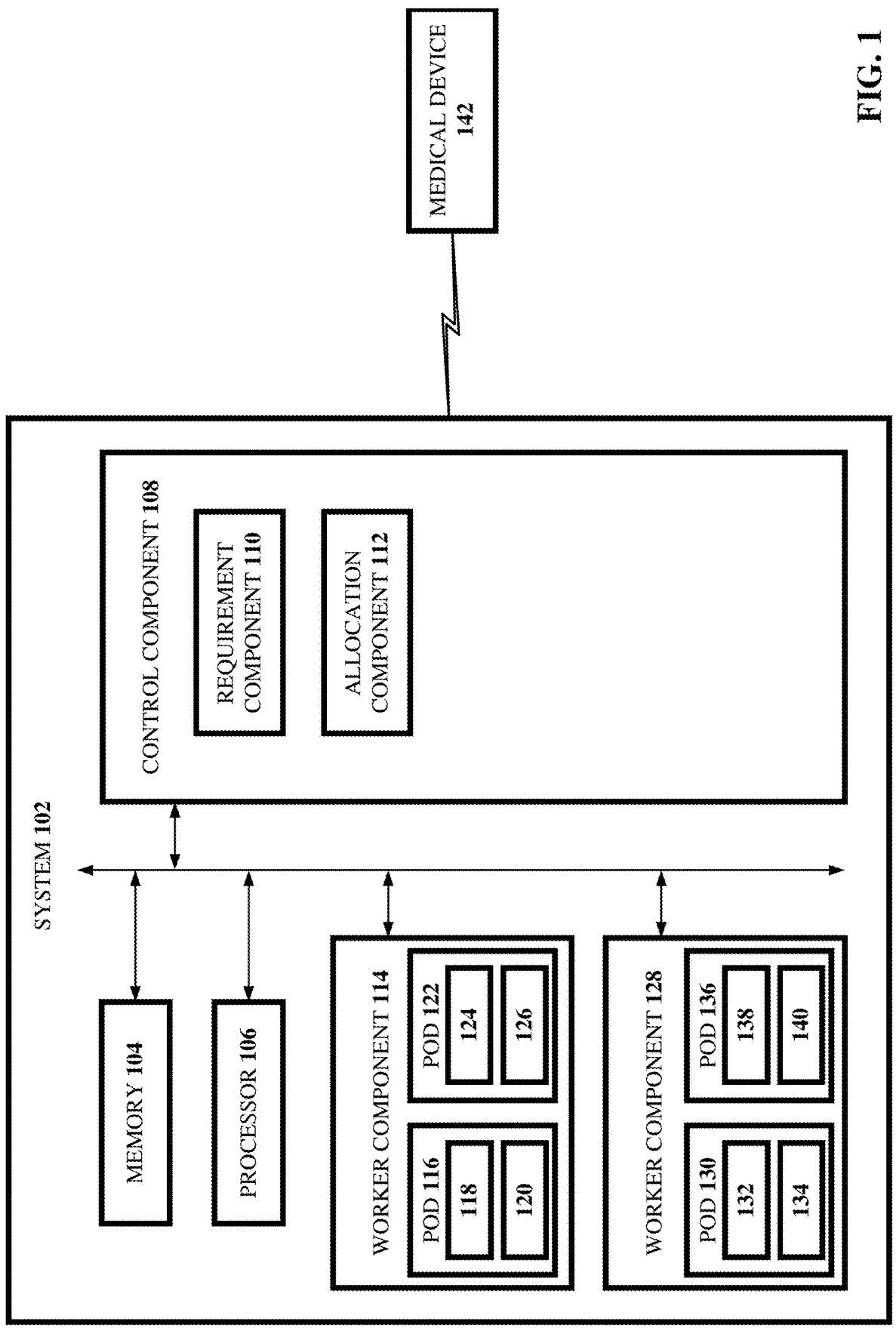
FIG. 1 is a block diagram of an exemplary system in accordance with one or more embodiments described herein.

The subject disclosure is now described with reference to the drawings, wherein like reference numerals are used to refer to like elements throughout. In the following description, for purposes of explanation, numerous specific details are set forth in order to provide a thorough understanding of the subject disclosure. It may be evident, however, that the subject disclosure may be practiced without these specific details. In other instances, well-known structures and devices are shown in block diagram form in order to facilitate describing the subject disclosure.

As alluded to above, medical software platforms can be improved in various ways, and various embodiments are described herein to this end and/or other ends.

Embodiments herein can utilize cloud technology and/or Kubernetes systems/structures to scale respective up/down in size or capability, depending on medical facility requirements. Kubernetes herein can be leveraged to host containerized medical applications (e.g., medical software applications) and can provide an API data model framework around which containerized services can be orchestrated. In various embodiments, by using architectures or systems as described herein, application development and deployment can be simplified, at least by providing core services for medical applications. It is noted that such medical applications can comprise medical software applications, verified and validated according to one or more clinical regularity and/or facility requirements.

Embodiments leveraging architectures described herein can provide increased patient safety and effectiveness to support medical device(s) with scalable services (e.g., using shared compute resources). In this regard, systems herein can be increased or decreased in size (e.g., computing capability and/or physical components) depending on application hosting requirements (e.g., quantity of medical applications hosted and/or aggregated computing demand). In this regard, embodiments herein enable vertically and horizontally scalable architectures for clinical systems and applications.

In an embodiment, a system can comprise a processor, and a memory that stores executable instructions that, when executed by the processor, facilitate performance of operations, comprising determining requirement information representative of one or more requirements of a medical application of a group of medical applications, wherein the medical application is associated with a medical device, based on the requirement information, allocating elements of a cluster employable to host and run the medical application in a medical application container, wherein the elements of the cluster are determined to satisfy the requirement information, and in response to allocating the elements of the cluster, hosting the medical application in the medical application container, wherein hosting the medical application comprises communicatively coupling the medical application to the medical device.

In various embodiments, allocating the elements of the cluster can comprise allocating redundant elements to host and run the medical application.

In some embodiments, the elements of the cluster can comprise one or more hosts, and allocating redundant elements to host and run the medical application can comprise allocating at least one extra host to host and run the medical application in a medical application container in addition to a minimum quantity of hosts determined, based on the requirement information, to be required to host and run the medical application in the medical application container.

In one or more embodiments, the above operations can further comprise in response to receiving medical data from the medical device, determining, based on the medical data, a destination application for the medical data. In this regard, the destination application can be determined to be the medical application.

It is noted that the cluster can be distributed across a first server located at a customer site and a second server located at a cloud storage site. In this regard, the customer site can be different from the cloud storage site. For example, a customer site can be located in city A, and the cloud storage site can be located in city B.

In an embodiment, the above operations can further comprise in response to receiving update data representative of an update to the medical application, applying the update data across the cluster. For instance, version 1.0 of a medical application can be updated to version 1.1 across a cluster hosting the medical application.

It is noted that the medical device can comprise an international electrotechnical commission (IEC) 62304 Class C medical device. It is noted that the medical device can comprise other IEC 62304 medical devices, such as IEC 62304 class A and/or IEC 62304 class B.

In some embodiments, the cluster can comprise a containerized machine learning service employable by the medical application to facilitate machine learning operations associated with the medical application. In further embodiments, the cluster can comprise a containerized digital imaging and communications in medicine (DICOM) service employable by the medical application to facilitate medical imaging operations associated with the medical application. In additional embodiments, the medical application can comprise a verified and validated medical application according to a clinical regularity requirement.

In another embodiment, a non-transitory machine-readable medium can comprise executable instructions that, when executed by a processor, facilitate performance of operations, comprising determining requirement information representative of one or more requirements of a medical application of a group of medical applications, wherein the medical application is associated with a medical device, based on the requirement information, allocating elements of a cluster employable to host and run the medical application in a medical application container, wherein the elements of the cluster are determined to satisfy the requirement information. and in response to allocating the elements of the cluster, hosting the medical application in the medical application container, wherein hosting the medical application comprises communicatively coupling the medical application to the medical device.

In various embodiments, the elements of the cluster can comprise two or more hosts (e.g., Kubernetes worker components), and the above operations can further comprise balancing computing associated with the medical application across the two or more hosts. In this regard, each host of the two or more hosts can operate a replica of the medical application in a respective medical application container.

In some embodiments, the above operations can further comprise allocating at least one redundant host, of the two or more hosts, to host and run the medical application in a medical application container in addition to a minimum quantity of hosts determined, based on the requirement information, to be required to host and run the medical application in the medical application container.

It is noted that the two or more hosts can comprise two or more virtual machines, and the above operations can further comprise generating, using a hypervisor, the two or more virtual machines based on the requirement information.

In one or more embodiments, the above operations can further comprise in response to receiving medical data from the medical device, determining, based on the medical data, destination applications for the medical data from among the group of medical applications, wherein the destination applications comprise the medical application.

In yet another embodiment, a method can comprise determining, by distributed medical software platform hosting equipment comprising a processor, requirement information representative of one or more requirements of a medical application of a group of medical applications, wherein the medical application is associated with a medical device, based on the requirement information, allocating, by the distributed medical software platform hosting equipment, elements of a cluster employable to host and run the medical application in a medical application container, wherein the elements of the cluster are determined to satisfy the requirement information, and in response to allocating the elements of the cluster, hosting, by the distributed medical software platform hosting equipment, the medical application in the medical application container, wherein hosting the medical application comprises communicatively coupling the medical application to the medical device.

In some embodiments, the method can further comprise allocating, by the distributed medical software platform hosting equipment, a group of hosts comprising at least one redundant host to host and run the medical application in a medical application container in addition to a minimum quantity of hosts determined, based on the requirement information, to be required to host and run the medical application in the medical application container.

In one or more embodiments, the method can further comprise removing, from the group of hosts, by the distributed medical software platform hosting equipment, a host in response to a host removal criterion being determined to be satisfied. It is noted that in various embodiments, the host removal criterion can comprise a maintenance criterion. In further embodiments, the host removal criterion can comprise a performance criterion.

To the accomplishment of the foregoing and related ends, the disclosed subject matter, then, comprises one or more of the features hereinafter more fully described. The following description and the annexed drawings set forth in detail certain illustrative aspects of the subject matter. However, these aspects are indicative of but a few of the various ways in which the principles of the subject matter can be employed. Other aspects, advantages, and novel features of the disclosed subject matter will become apparent from the following detailed description when considered in conjunction with the provided drawings.

It should be appreciated that additional manifestations, configurations, implementations, protocols, etc. can be utilized in connection with the following components described herein or different/additional components as would be appreciated by one skilled in the art.

Turning now to FIG. 1, there is illustrated an example, non-limiting system 102 in accordance with one or more embodiments herein. System 102 can comprise a computerized tool, which can be configured to perform various operations relating to distributed medical software platforms. The system 102 can comprise one or more of a variety of components, such as memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, and/or medical device 142.

In various embodiments, one or more of the memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, and/or medical device 142 can be communicatively or operably coupled (e.g., over a bus or wireless network) to one another to perform one or more functions of the system 102.

According to an embodiment, system 102 can comprise a physical machine (e.g., a server) which can comprise physical computer resources. Each physical resource can provide one or more compute accelerators (e.g., graphics processing units, field programmable gate arrays, or other suitable components), one or more standard compute chips (e.g., central processing unit), one or more measures of memory (e.g., random access memory), one or more measures of storage (e.g., disks or solid state drives), one or more network interfaces (e.g., network interface cards). According to an embodiment, the control component 108 can comprise a hypervisor, which can generate one or more virtual machines based on requirement information. A compute fabric layer can be enabled by the system 102 through the addition of a hypervisor layer. In this regard, a hypervisor layer can enable host of virtual machines (e.g., software-defined computers). Each software-defined computer (e.g., virtual machines) can be assigned a defined quantity of compute resources, the use of can be facilitated by the hypervisor layer. One or more virtual machines can be installed in a system 102, and can be configured to function as a distributed container orchestration cluster (e.g., Kubernetes or another suitable cluster).

In another embodiment, the system 102 can comprise a virtual machine with virtualized resources (e.g., virtualized physical computer resources). Such resources can comprise one or more of a hypervisor, Kubernetes cluster, virtual machine, operating system (OS), software defined storage, load balancer, gateway, router, system services, network interface or other suitable resources.

As alluded to above, various resources herein can comprise physical components or computer executable components. It is noted that one or more components of the system 102 can comprise elements of a cluster (e.g., a Kubernetes cluster). For example, a cluster herein can comprise a Kubernetes (k8s) container system which can comprise a plurality of nodes (e.g., worker components such as worker component 114 or worker component 128). Each node or worker component can comprise a container runtime (e.g., Docker) or a Pod (e.g., a group of containers or Dockers). Various platform services can be executed within a control component 108, worker component (e.g., worker component 114 and/or worker component 128), pod (e.g., pod 116, pod 122, pod 130, and/or pod 136), or container herein, such as software-defined storage providing dynamically provisioned storage slices from an overall pool of common storage, system and application telemetry services providing visibility to the current and past metrics and events occurring within the system 102 and associated applications, system and application security services providing identity, authentication, and access control to the system and applications, database management capabilities providing applications a structured persistent state, or other suitable services.

In various embodiment, the system 102 can host medical applications via containers (e.g., containers 118, 120, 124, 126, 132, 134, 138, or 140), or virtual machines (not depicted). Medical applications and services herein can utilize one or more containers, which work together as a single unit (e.g., a pod) which can be hosted in a platform container orchestration cluster. Applications that utilize of one or more virtual machines can be hosted on a system hypervisor layer (see, e.g., FIGS. 6 and 8-10).

According to an embodiment, the system 102 can be resized to comprise more or less virtual compute capability, in the form of virtual machines, to run containerized medical applications. For example, more virtual machines can be added to the container orchestration cluster to accommodate running additional container-based applications.

According to an embodiment, the control component 108 can comprise a requirement component 110 and allocation component 112. It is noted that the control component 108 can comprise a control plane, which can be configured to manage one or more worker components (e.g., worker component 114, worker component 128, or other worker components not depicted herein). In an embodiment, the control component 108 (e.g., using the requirement component 110) can determine requirement information representative of one or more requirements of a medical application (e.g., from a group of medical applications). Such requirements can comprise one or more of processing power, graphics processing power, memory, storage, audio hardware, API, driver, virtual machines, OS, hypervisor, peripherals or other physical hardware, network connectivity, worker nodes or hosts, containers, services, or other suitable requirements. Such requirements can be based on specifications set forth in a respective medical application, or can be determined, for instance, based on a machine learning analysis of the respective medical application.

According to an embodiment, the control component 108 (e.g., using the allocation component 112) can, based on said requirement information, allocate elements of a cluster (e.g., cluster hosts comprising the worker component 114 and worker component 128) employable to host and run the medical application in a medical application container (e.g., one or more of container 118, container 120, container 124, container 126, container 132, container 134, container 138, container 140, or other suitable containers). In this regard, the elements of the cluster can be determined (e.g., by the control component 108) to satisfy the requirement information.

In various embodiments herein, clusters can be distributed across one or more servers (e.g., server 614 as later discussed). For example, a cluster can be distributed across a server located at a customer site and a server located at a cloud storage site. In this regard, a compute fabric layer can be provided as part of the system 102 or by a third party (e.g., a cloud provider).

It is noted that elements of the cluster comprise one or more hosts (e.g., worker components 114 and/or 128), and allocating elements of the cluster (e.g., by the allocation component 112) can comprise allocating redundant element(s) to host and run the medical application. In this regard, allocating redundant elements (e.g., worker components 114 and/or 128) to host and run the medical application can comprise allocating at least one extra host (e.g., worker component 114 and/or 128) to host and run the medical application in a medical application container, in addition to a minimum quantity of hosts determined (e.g., by the control component 108), based on the requirement information, to be required to host and run the medical application in the medical application container. In this regard, N+1 worker components (e.g., hosts) can be utilized to host and run a medical application, in which N represents the minimum quantity of worker components (e.g., hosts) to host and run the medical application in a medical application container herein. For example, additional worker components can be added to a compute fabric if additional medical applications are to be hosted on the platform, either in the form of container-based applications or virtual machine based applications. In other embodiments, worker components can comprise N+1 resources, such as network interfaces, storage, CPUs, accelerators, GPUs, or other suitable resources.

According to an embodiment, in response to the allocation component 112 allocating the elements of the cluster, the control component 108 can cause one or more worker components (e.g., 114 and/or 128) to host the medical application in a respective medical application container herein. In various embodiments, hosting the medical application can comprise communicatively coupling the medical application to a medical device 142. In various embodiments, the medical device 142 can comprise an international electrotechnical commission (IEC) 62304 Class C medical device. In this regard, a medical device 142 can send or receive data from said communicatively coupled medical application.

Worker components herein (e.g., worker component 114, worker component 128, or other worker components not depicted) can comprise pods (e.g., pod 116, pod 122, pod 130, pod 136, or other pods) which can comprise deployable units (e.g., groups) of containers. Pods herein can be resized to contain more containers or fewer containers. Containers herein can comprise a variety of medical applications and/or services. For instance, a cluster herein can comprise a container which can comprise a containerized machine learning service employable by a medical application to facilitate machine learning operations associated with the medical application. In this regard, the medical application itself need not comprise its own machine learning service, and can instead leverage the containerized machine learning service stored in a container within the system 102. In other embodiments, such a container can comprise a containerized digital imaging and communications in medicine (DICOM) service employable by the medical application to facilitate medical imaging operations associated with the medical application. In this regard, the medical application itself need not comprise its own DICOM service. Likewise, such a container can comprise a workflow management service, and thus the medical application itself need not comprise its own workflow management service.

Various embodiments herein can employ artificial-intelligence or machine learning systems and techniques to facilitate learning user behavior, context-based scenarios, preferences, etc. in order to facilitate taking automated action with high degrees of confidence. Utility-based analysis can be utilized to factor benefit of taking an action against cost of taking an incorrect action. Probabilistic or statistical-based analyses can be employed in connection with the foregoing and/or the following.

It is noted that systems and/or associated controllers, servers, or machine learning components herein can comprise artificial intelligence component(s) which can employ an artificial intelligence (AI) model and/or machine learning or a machine learning model that can learn to perform the above or below described functions (e.g., via training using historical training data and/or feedback data).

In some embodiments, an AI and/or ML model can be trained (e.g., via supervised and/or unsupervised techniques) to perform the above or below-described functions using historical training data comprising various context conditions that correspond to various augmented network optimization operations. In this example, such a model can further learn (e.g., via supervised and/or unsupervised techniques) to perform the above or below-described functions using training data comprising feedback data, where such feedback data can be collected and/or stored (e.g., in memory). In this example, such feedback data can comprise the various instructions described above/below that can be input, for instance, to a system herein, over time in response to observed/stored context-based information.

Components herein leveraging AI/machine learning (e.g., the control component 108) can initiate an operation(s) associated with a based on a defined level of confidence determined using information (e.g., feedback data). For example, based on learning to perform such functions described above using feedback data, performance information, and/or past performance information herein, a control component 108 or other suitable components described herein can initiate an operation associated with determining various thresholds or criterion herein.

In an embodiment, the control component 108 or other suitable components herein can perform a utility-based analysis that factors cost of initiating the above-described operations versus benefit. In this embodiment, one or more components herein can use one or more additional context conditions to determine various thresholds herein.

To facilitate the above-described functions, a one or more components herein can perform classifications, correlations, inferences, and/or expressions associated with principles of artificial intelligence. For instance, one or more components herein can employ an automatic classification system and/or an automatic classification. In one example, the one or more components herein can employ a probabilistic and/or statistical-based analysis (e.g., factoring into the analysis utilities and costs) to learn and/or generate inferences. One or more components herein can employ any suitable machine-learning based techniques, statistical-based techniques and/or probabilistic-based techniques. For example, the one or more components herein can employ expert systems, fuzzy logic, support vector machines (SVMs), Hidden Markov Models (HMMs), greedy search algorithms, rule-based systems, Bayesian models (e.g., Bayesian networks), neural networks, other non-linear training techniques, data fusion, utility-based analytical systems, systems employing Bayesian models, and/or the like. In another example, one or more components herein can perform a set of machine-learning computations. For instance, one or more components herein can perform a set of clustering machine learning computations, a set of logistic regression machine learning computations, a set of decision tree machine learning computations, a set of random forest machine learning computations, a set of regression tree machine learning computations, a set of least square machine learning computations, a set of instance-based machine learning computations, a set of regression machine learning computations, a set of support vector regression machine learning computations, a set of k-means machine learning computations, a set of spectral clustering machine learning computations, a set of rule learning machine learning computations, a set of Bayesian machine learning computations, a set of deep Boltzmann machine computations, a set of deep belief network computations, and/or a set of different machine learning computations.

Figure 2:
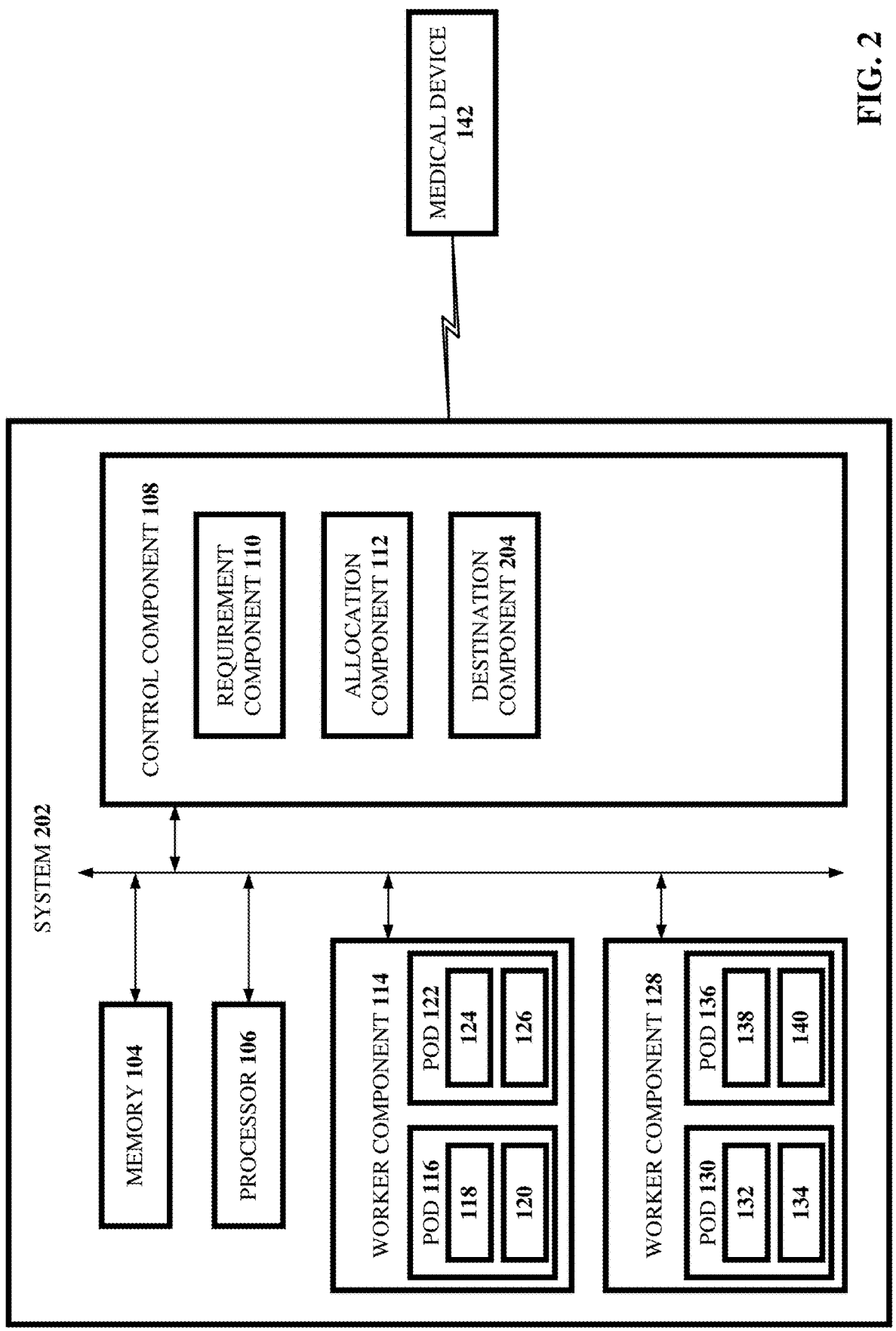
FIG. 2 is a block diagram of an exemplary system in accordance with one or more embodiments described herein.

Turning now to FIG. 2, there is illustrated an example, non-limiting system 202 in accordance with one or more embodiments herein. System 202 can comprise a computerized tool, which can be configured to perform various operations relating to distributed medical software platforms. The system 202 can be similar to system 102, and can comprise one or more of a variety of components, such as memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, and/or medical device 142. The system 202 can additionally comprise a destination component 204.

In various embodiments, one or more of the memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, and/or destination component 204 can be communicatively or operably coupled (e.g., over a bus or wireless network) to one another to perform one or more functions of the system 202.

According to an embodiment, the destination component 204 can, in response to receiving medical data from the medical device 142, determine, based on the medical data, a destination medical application (e.g., of a group of medical applications) for the medical data. In this regard, the system 202 can be communicatively coupled to a plurality of medical devices 142 and can receive medical data from the plurality of medical devices. Likewise, the system 102 can host a plurality of medical applications. In this regard, the destination component 204 can analyze the medical data in order to determine the medical application(s) to provide the medical data. For instance, the destination component can receive DICOM medical data from a medical imaging scanner (e.g., CT scanner, X-Ray scanner, MRI scanner, PET Scanner, ultrasound, or another suitable medical imaging scanner) and provide the DICOM medical data to a medical imaging application. In other embodiments, such medical data comprise various waveforms, numeric data, alarms, sensor outputs, or other suitable medical data. It is noted that the destination component 204 can determine a destination medical application based on the type of medical data received. In other embodiments, the destination component 204 can utilize machine learning in order to determine the destination application(s) based on the medical data received and/or previously received medical data. In some embodiments, output from a single medical device 142 can be transmitted (e.g., using the destination component 204) to a plurality of medical applications. In other embodiments, medical data from a plurality of medical devices 142 can be transmitted (e.g., using the destination component 204) to a single medical application.

Figure 3:
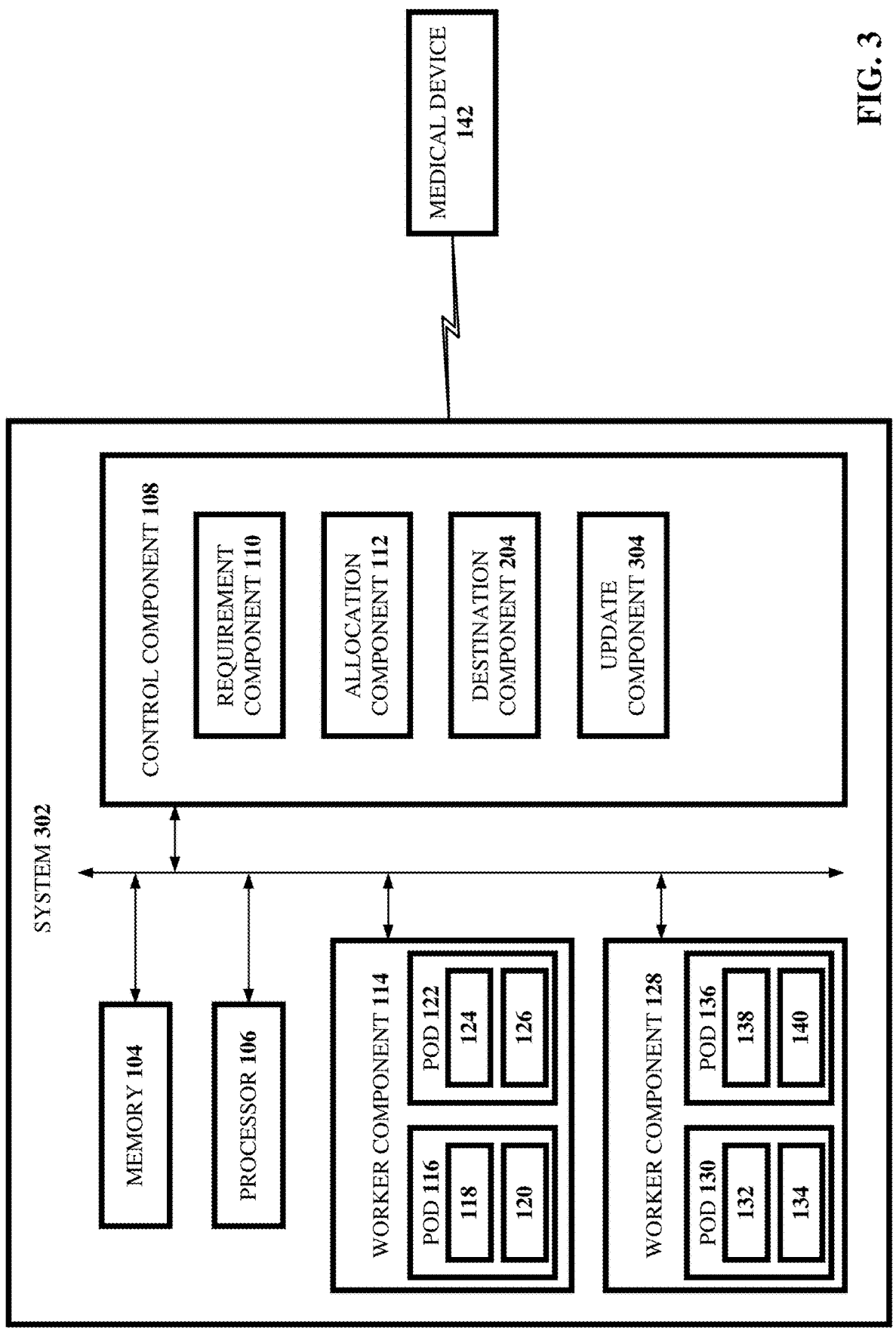
FIG. 3 is a block diagram of an exemplary system in accordance with one or more embodiments described herein.

Turning now to FIG. 3, there is illustrated an example, non-limiting system 302 in accordance with one or more embodiments herein. System 302 can comprise a computerized tool, which can be configured to perform various operations relating to distributed medical software platforms. The system 302 can be similar to system 202, and can comprise one or more of a variety of components, such as memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, and/or destination component 204. The system 302 can additionally comprise an update component 304.

In various embodiments, one or more of the memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, destination component 204, and/or update component 304 can be communicatively or operably coupled (e.g., over a bus or wireless network) to one another to perform one or more functions of the system 302.

According to an embodiment, the update component 304 can, in response to receiving update data representative of an update to the medical application, apply the update data across the cluster. In this regard, medical applications herein can be updated with software updates, and said software updates can be implemented at each instance of the containerized medical application. For example, said update can be provided pod by pod, or container by container, at each worker component. In this regard, individual containers and/or worker components herein can be removed from a cluster (e.g., one at a time) to update the medical application, such that a minimum quantity of compute capability to host and run a medical application herein is maintained. The foregoing can be facilitated, for instance, using a removal component (e.g., removal component 504 as later discussed in greater detail).

Figure 4:
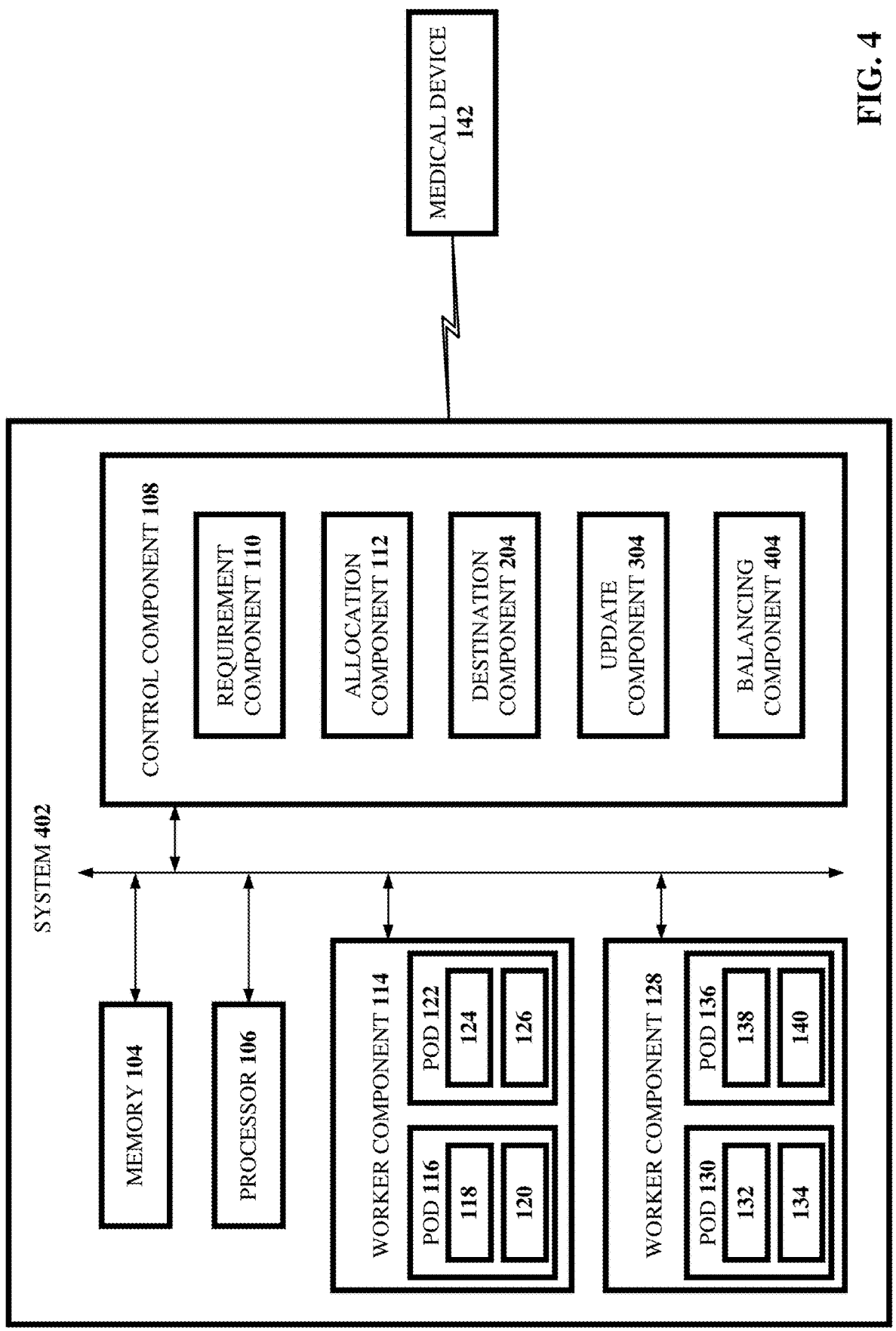
FIG. 4 is a block diagram of an exemplary system in accordance with one or more embodiments described herein.

Turning now to FIG. 4, there is illustrated an example, non-limiting system 402 in accordance with one or more embodiments herein. System 402 can comprise a computerized tool, which can be configured to perform various operations relating to distributed medical software platforms. The system 402 can be similar to system 302, and can comprise one or more of a variety of components, such as memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, destination component 204, and/or update component 304. The system 402 can additionally comprise a balancing component 404.

In various embodiments, one or more of the memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, destination component 204, update component 304, and/or balancing component 404 can be communicatively or operably coupled (e.g., over a bus or wireless network) to one another to perform one or more functions of the system 402.

According to an embodiment, the balancing component 404 can balance computing associated with a medical application across two or more hosts (e.g., worker components). In this regard, each worker component can operate a replica of the medical application in a respective medical application container. For example, a medical device 142 can output data to be processed by a medical application herein. In this regard, processing of said data can be shared by multiple instances of the medical application running on respective worker components herein, which can expedite processing of said data and/or provide data processing redundancy.

Figure 5:
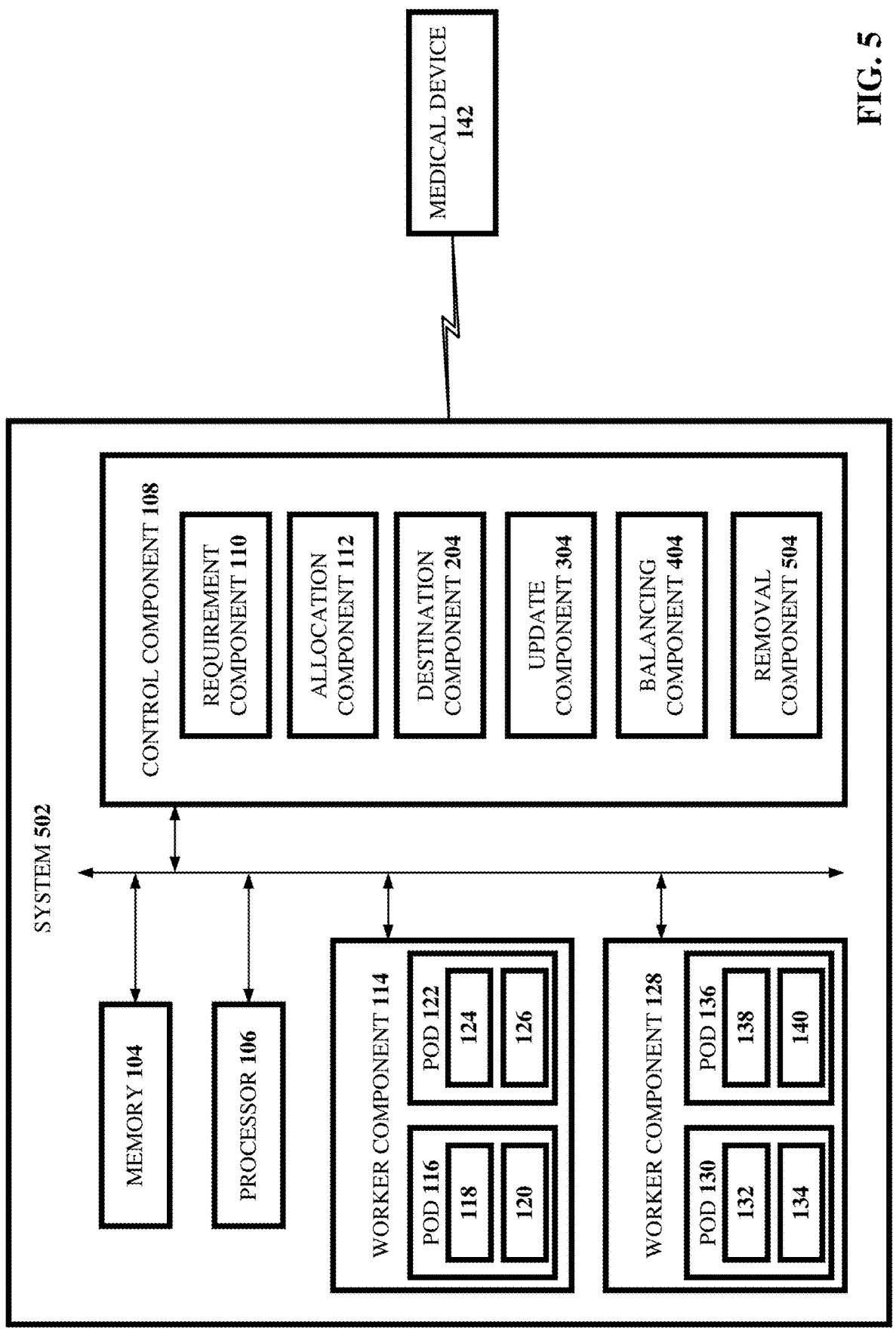
FIG. 5 is a block diagram of an exemplary system in accordance with one or more embodiments described herein.

Turning now to FIG. 5, there is illustrated an example, non-limiting system 502 in accordance with one or more embodiments herein. System 502 can comprise a computerized tool, which can be configured to perform various operations relating to distributed medical software platforms. The system 502 can be similar to system 402, and can comprise one or more of a variety of components, such as memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, destination component 204, update component 304, and/or balancing component 404. The system 502 can additionally comprise a removal component 504.

In various embodiments, one or more of the memory 104, processor 106, control component 108, requirement component 110, allocation component 112, worker component 114, pod 116, container 118, container 120, pod 122, container 124, container 126, worker component 128, pod 130, container 132, container 134, pod 136, container 138, container 140, medical device 142, destination component 204, update component 304, balancing component 404, and/or removal component 504 can be communicatively or operably coupled (e.g., over a bus or wireless network) to one another to perform one or more functions of the system 502.

According to an embodiment, the removal component 504 can remove, from a host from a group of hosts (e.g., worker components herein), response to a host removal criterion being determined (e.g., by the removal component 504) to be satisfied. For example, such a removal criterion can comprise a maintenance criterion (e.g., a maintenance schedule). In another example, such a removal criterion can comprise a performance criterion (e.g., a performance threshold). As previously discussed, a worker component and/or container herein can be removed (e.g., by the removal component 504) in order to update a medical application herein.

It is noted that various systems and architectures herein can comprise, or be communicatively coupled to, hardware required to implement a variety of communication protocols (e.g., infrared ("IR"), shortwave transmission, near-field communication ("NFC"), Bluetooth, Wi-Fi, long-term evolution ("LTE"), 3G, 4G, 5G, 6G, global system for mobile communications ("GSM"), code-division multiple access ("CDMA"), satellite, visual cues, radio waves, etc.)

Figure 6:
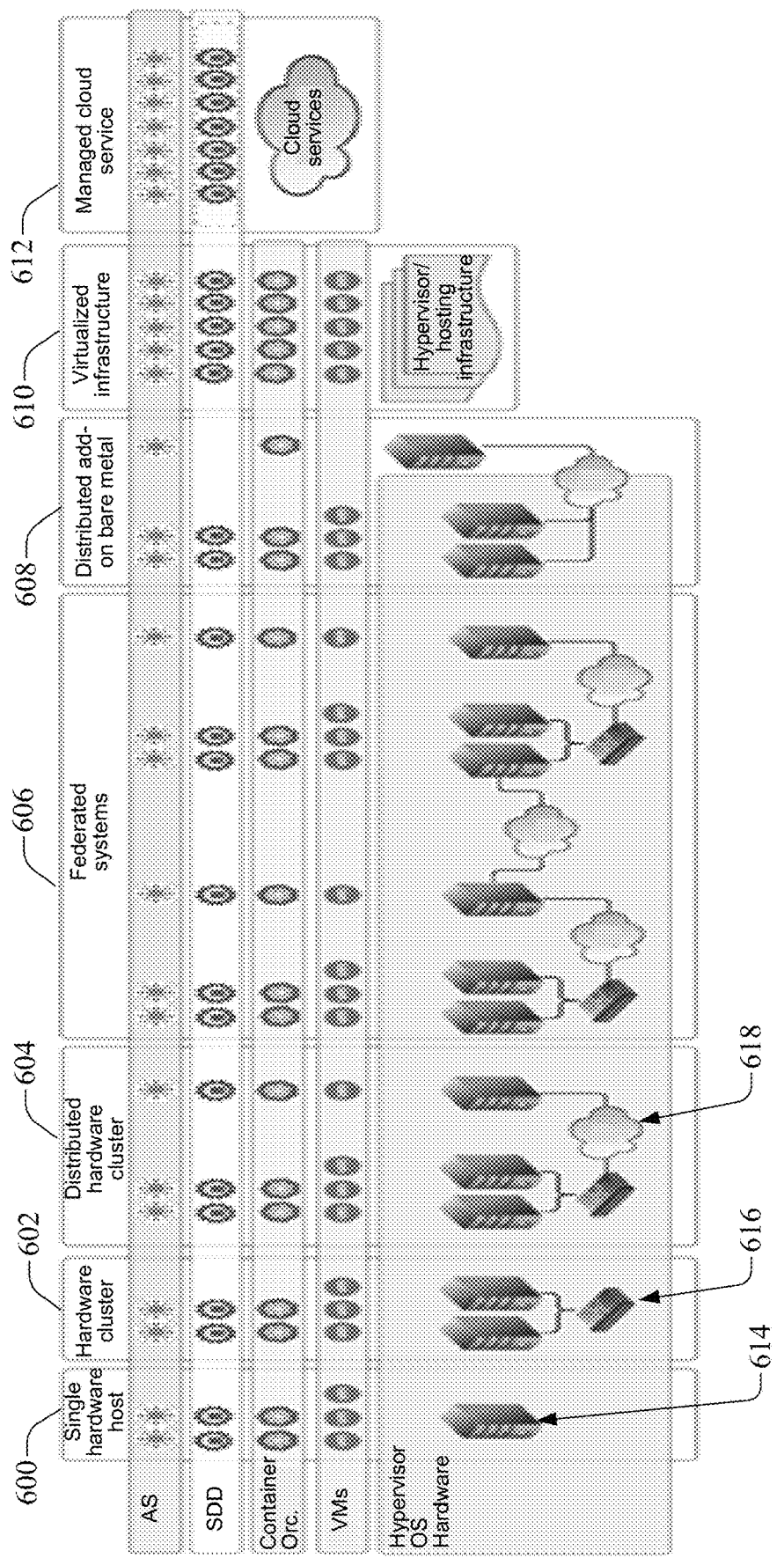
FIG. 6 illustrates a diagram of exemplary system architectures in accordance with one or more embodiments described herein.

With reference to FIG. 6, there are illustrated architectures 600, 602, 604, 606, 608, 610, and 612. Such architectures illustrate a range of various embodiments herein comprising a variety of components. For instance, architecture 600 comprises a single hardware host. In this regard, architecture 600 can comprise a single server 614 (e.g., hypervisor OS hardware). Such a server 614 can comprise a plurality of virtual machines. In FIG. 6, "AS" corresponds to architecture and services, "SDD" corresponds to software defined storage, and "container orc." corresponds to container orchestration.

According to an example, a server can comprise ten virtual machines. In this regard, one or more of the ten virtual machines can be part of a Kubernetes cluster. For instance, eight of the ten virtual machines can be nodes in a Kubernetes cluster. The foregoing Kubernetes cluster can enable software-defined storage and services/applications hosted on the Kubernetes cluster. In an embodiment, architecture 600 can comprise a foundation of a system (e.g., with capacity for expansion) in accordance with other embodiments herein.

Architecture 602 can comprise components similar to architecture 600. For example, architecture 602 can comprise a plurality of servers 614 connected with a switch 616 with each server comprising a plurality of virtual machines. Any of such virtual machines can comprise nodes (e.g., control components, worker components, or hosts herein) in a Kubernetes cluster for enabling software-defined storage and services or applications hosted in the Kubernetes cluster. According to an embodiment, virtual machines can interface with a hypervisor herein with a one-to-one relationship, such that adding more physical servers 614 into a physical system (e.g., a system 102) does not impact (e.g., alter processing capabilities) existing virtual machines. Rather, in an embodiment, the virtual machines only interact with respective hardware that the virtual machines require. In this regard, for example, by adding a second server 614, a corresponding system (e.g., system 102) can be doubled in size without changing or interrupting preexisting applications, services, or other system 102 components.

Architectures 604-612 can leverage additional networked servers to further increase the capacity of the Kubernetes cluster. For example, architecture 604 can comprise two or more servers 614 connected with a switch 616. In some embodiments, distributed servers 614 can be indirectly connected to the switch 616 (e.g., in a distributed cluster). According to an embodiment, in architecture 606, services can be cloud-located (e.g., via a shared network such as a cloud 618) and can be federated into a system as a set of services available as a single system (e.g., system 102). In this regard, a plurality of systems herein can cooperate with one another. For example, of one system requires additional compute capability, and another system has compute capability to spare, computing can be distributed accordingly across the systems. In architecture 608, an existing system can be coupled to additional hardware. According to an example, such additional hardware can be remotely located (e.g., at a customer site). Architecture 610 can utilize a hypervisor hosting environment (e.g., with a VMware cluster). In this regard, a system herein can be deployed atop an existing hosting environment. According to an embodiment, architecture 612 can be completely cloud managed. In this regard, physical hardware can be omitted, and a system herein (e.g., system 102) can be completely cloud hosted.

It is noted that architectures 604-612, in addition to other suitable architectures or systems described herein or omitted for sake of brevity, can enable a scalable infrastructure to host medical applications and software-based medical devices in a clinical context. Such scalability can enable vertical control such that a medical system can be more easily managed as opposed to legacy cloud-based environments. Further, systems herein can be rapidly and efficiently scaled horizontally, by adding more machines in the form of physical machines and/or virtual machines to host more applications.

Figure 7:
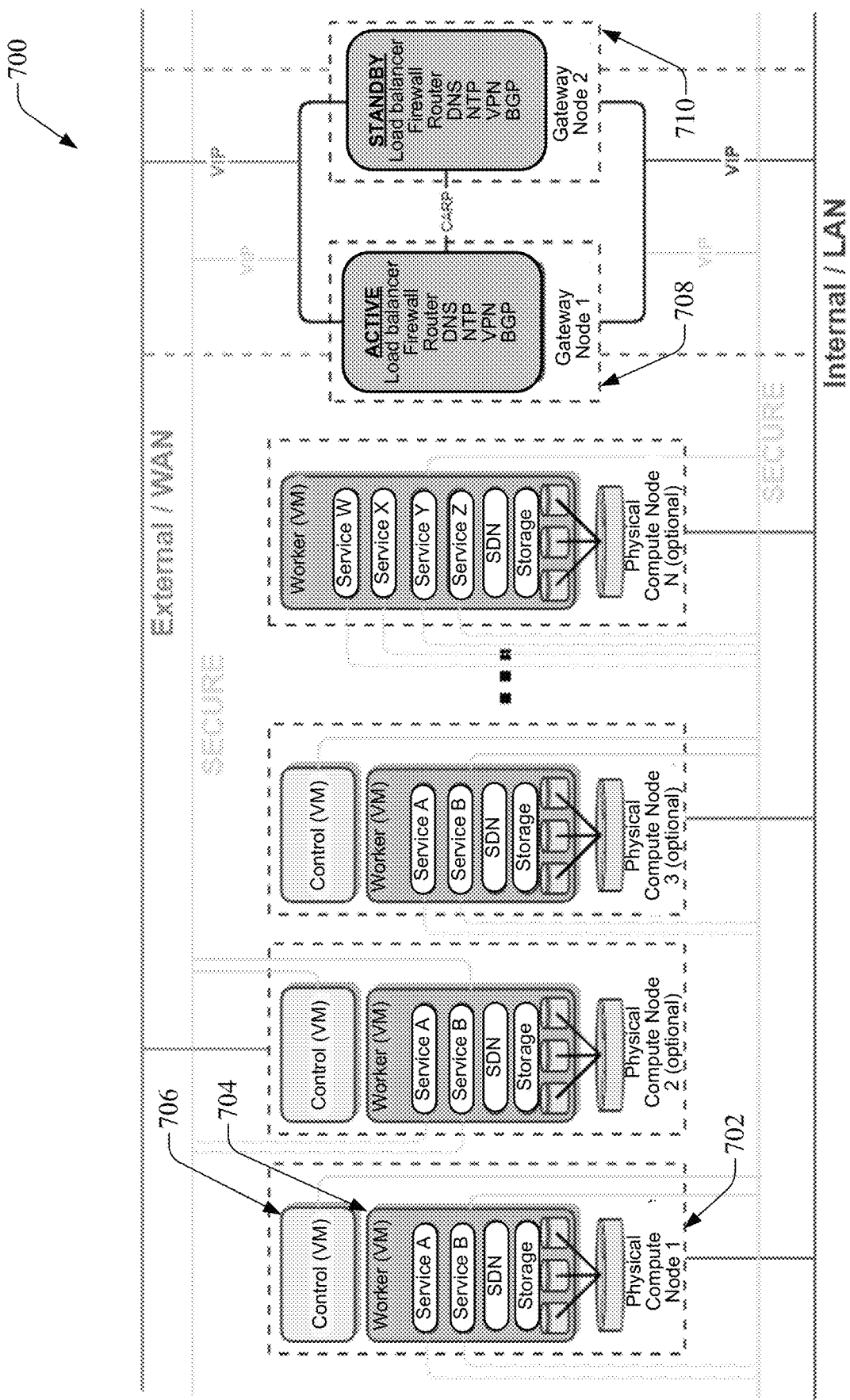
FIG. 7 illustrates a diagram of an exemplary system architecture in accordance with one or more embodiments described herein.

Turning now to FIG. 7, there is illustrated a communication topology architecture 700 in accordance with various embodiments herein. The architecture 700 can comprise a plurality of systems 702, which can each comprise one or more worker components 704 and control components 706. Each worker component 704 (e.g., a Kubernetes Worker virtual machine) can comprise applications/services in addition to infrastructure components such as storage and network components. Kubernetes clusters described herein can enable the architecture 700 to be implemented, for instance, in a self-contained data center, or implemented as a cloud-based infrastructure. Gateways 708 and 710 can enable respective traffic to flow in/out of architecture 700.

Figure 8:
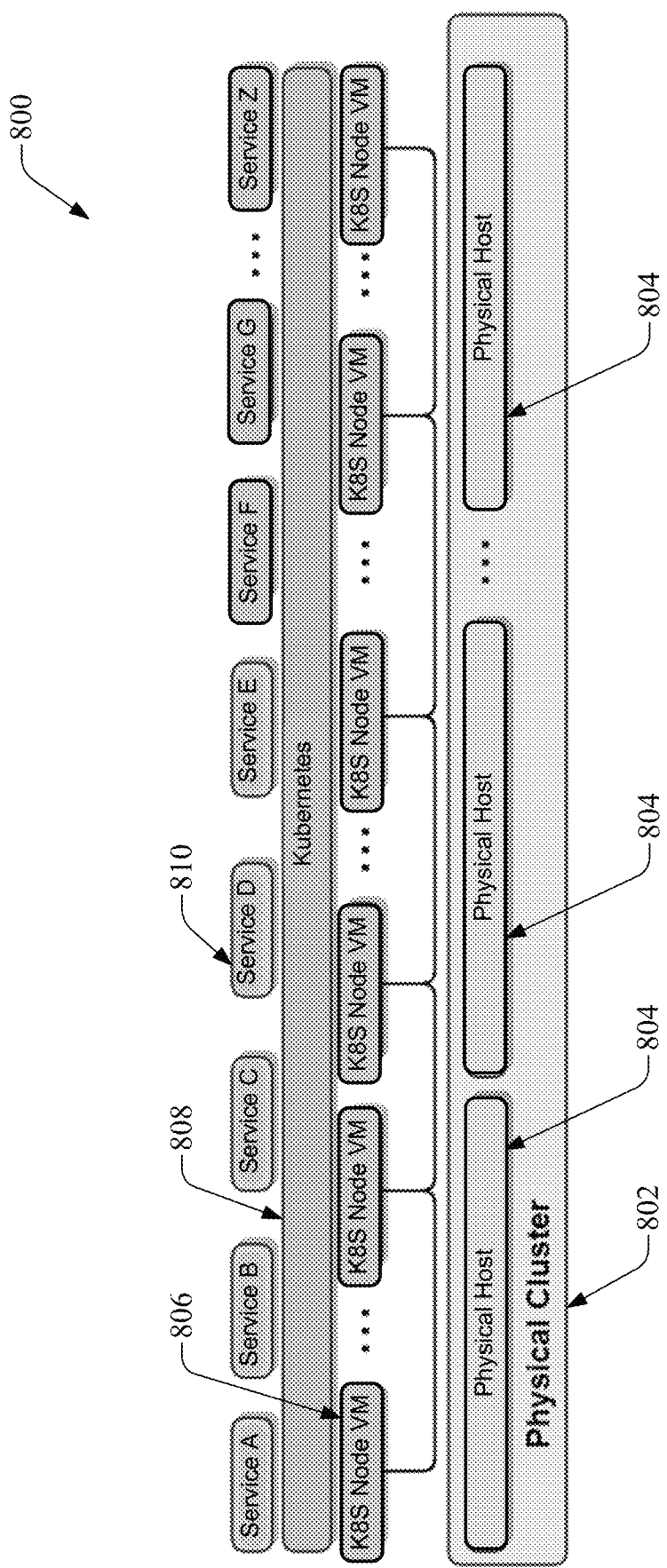
FIG. 8 illustrates a diagram of an exemplary system architecture topology in accordance with one or more embodiments described herein.
Figure 9:
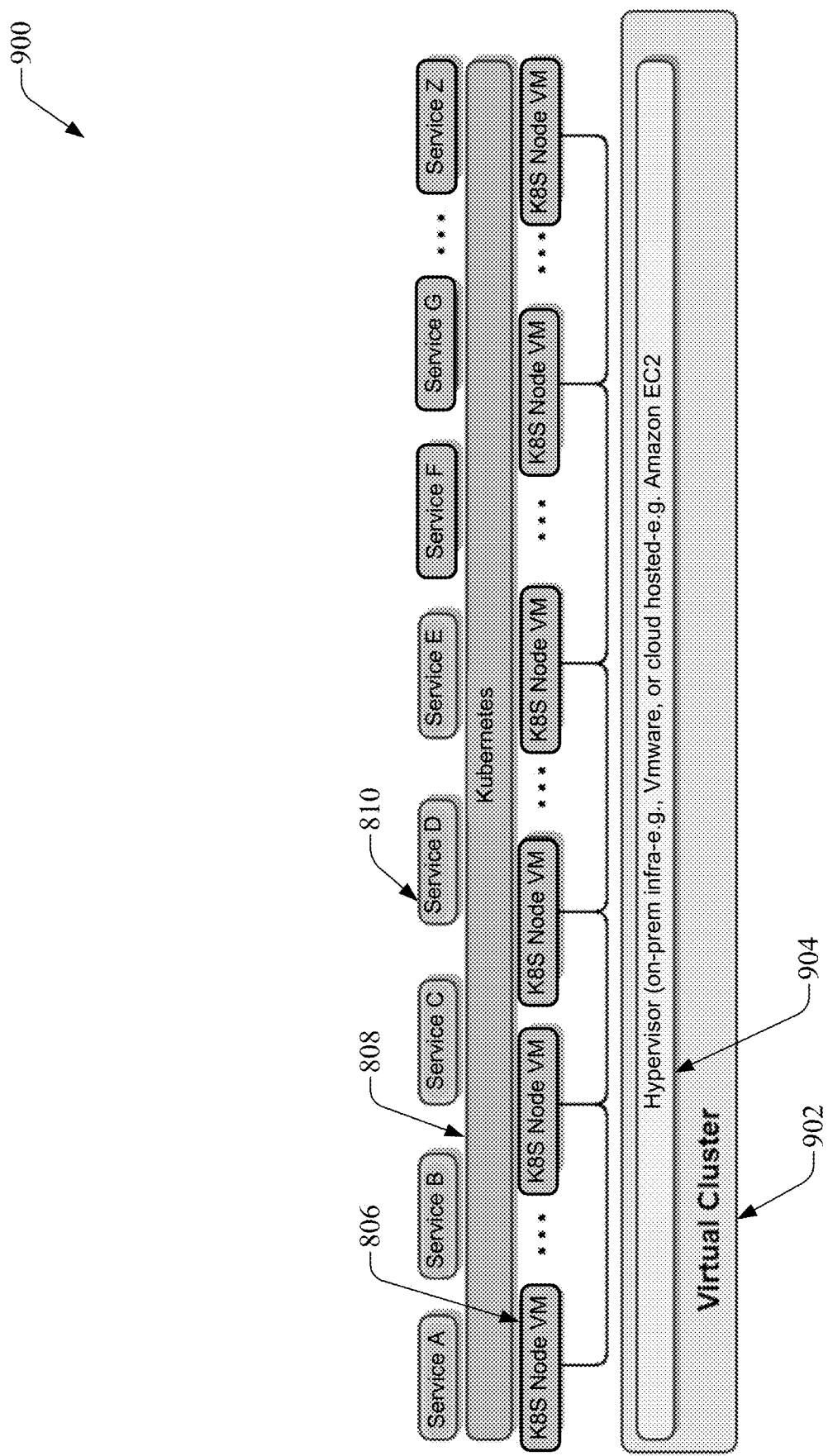
FIG. 9 illustrates a diagram of an exemplary system architecture topology in accordance with one or more embodiments described herein.
Figure 10:
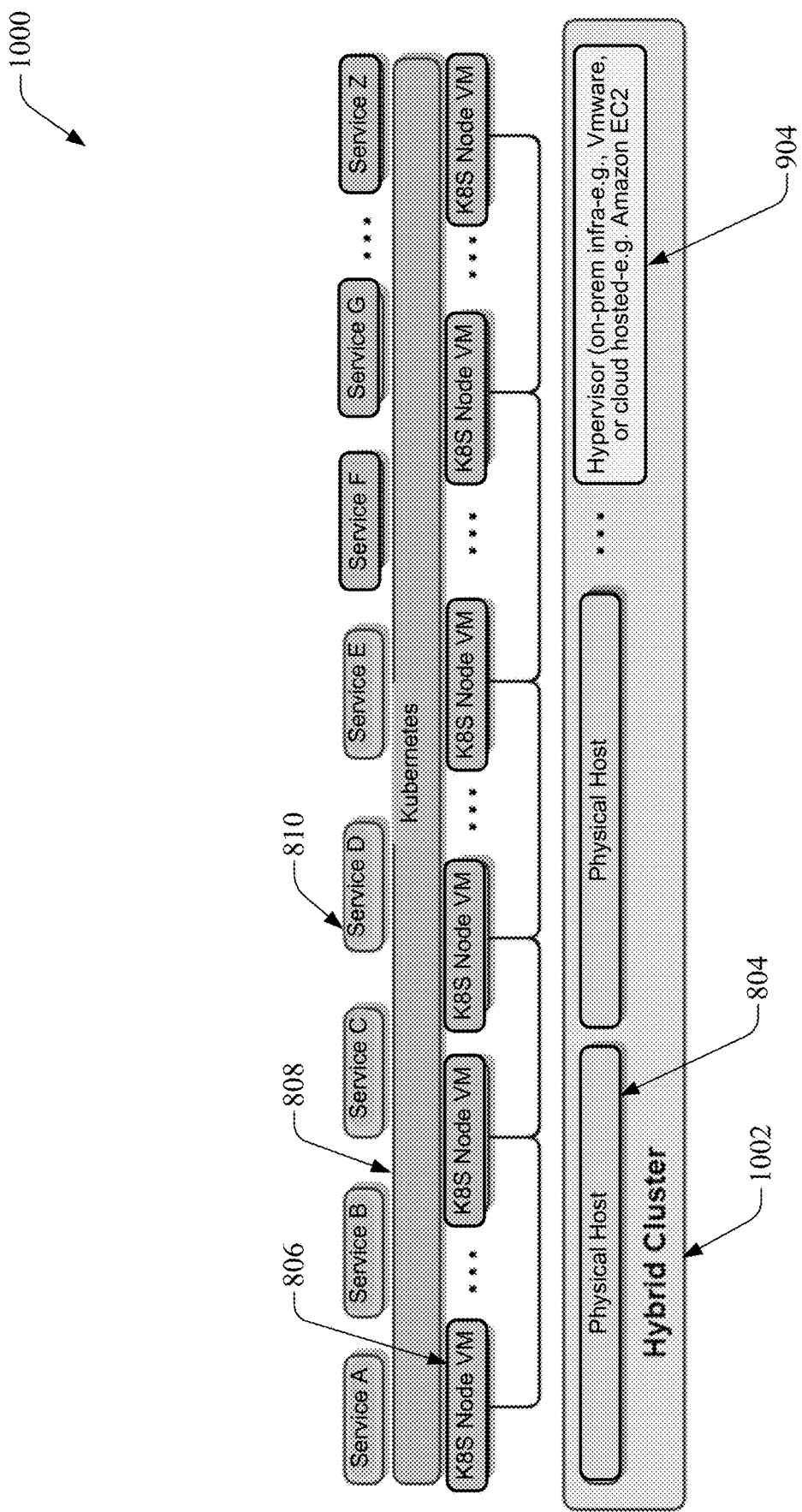
FIG. 10 illustrates a diagram of an exemplary system architecture topology in accordance with one or more embodiments described herein.

Turning now to FIGS. 8-10, there are illustrated topologies 800, 900, and 1000 in accordance with various embodiments herein. Topology 800 can comprise a physical cluster 802, topology 900 can comprise a virtual cluster 902, and topology 1000 can comprise a hybrid cluster 1002 comprising both physical and virtual cluster components and/or subcomponents. Physical cluster 802 can comprise one or more physical hosts 804 (e.g., server(s)). Such physical hosts 804 can comprise managed hardware or appliances, for instance, as implemented in a medical facility, and can host virtual machines (e.g., worker components and/or control components herein). Virtual cluster 902 can comprise a hypervisor 904 for hosting virtual machines described herein. Hybrid cluster 1002 can comprise a combination of physical host(s) 804 and hypervisor(s) 904. Each of the clusters 802, 902, and 1002 can comprise Kubernetes nodes. In this regard, a Kubernetes system herein can be leveraged to provide a singularity or plurality of varying services or applications. Examples of such applications or services can comprise medical imaging applications, surgical applications, patient monitoring applications, IT services, medicine delivery applications, or various other suitable applications or services relating to healthcare systems or medical devices.

It is noted that architectures and/or systems described herein can support a wide range of medical devices (e.g., medical device 142) and/or associated software, such as medical imaging, patient monitoring, electronic medical records, tele-medicine services, or other suitable hardware and associated software.

By utilizing systems and/or architectures described herein, rapid verification and validation can be conducted, at least because applications and services herein can leverage the Kubernetes structure, and entire systems need not be revalidated/reverified in response to an isolated modification in the system, upgrade, or other change. For example, a medical application can be validated. In this example, such a medical application can perform its requirements using a defined quantity of CPU cores and a defined amount of memory. If additional resources are added to an associated system, the medical application need not be revalidated/reverified despite system changes, for instance, because the medical application itself can operate in isolation in the environment in which testing was already conducted (e.g., by leveraging the Kubernetes containerized structure and/or via virtual machine(s)). In this regard, the impact of scaling a system can be abstracted away from an environment in which a verified/validated medical application runs. Further, a modification to one medical application does not impact another medical application by virtue of both medical applications leveraging Kubernetes hosting.

By leveraging a Kubernetes/cloud native platform, an associated system (e.g., system 102) can be modular, as hardware components described herein can be isolated from virtual components, and virtual components can be separated from Kubernetes, and Kubernetes can be separated from clinical services. In this regard, systems leveraging architectures described herein can deploy various layers that are abstracted from each other, such that systems herein can change or be enlarged in isolation from each other (e.g., adding more hardware without modifying anything running atop, adding more virtual machines without modifying underlying physical hardware, adding more services/applications without changing worker components) and can be deployed on existing hardware or on virtual machines. The foregoing provides a highly scalable architecture, thus enabling systems possessing scalability which can satisfy regulatory, performance, and/or reliability requirements inherent to the healthcare industry.

Systems leveraging architectures described herein can enable low-latency and high-consistency performance and/or reliability, as can be required in the medical context to meet various clinical requirements. In this regard, systems leveraging systems or architectures described herein can support low-latency, high-performance applications (e.g., medical applications), for instance, with priority scheduling. According to an embodiment, medical applications described herein can comprise various priorities relative to each other, and system resources herein can be allocated and/or adjusted with respect to such priorities. For example, such priorities can change in response to changes in medical and/or medical application requirements, or can be determined by machine-learning. In this regard, a system herein can leverage machine-learning to determine priorities based on various historical, present, and future clinical needs, clinical requirements, and/or system resources. Further in this regard, a system can self-identity its own limitations (e.g., compute capability, storage capacity, network throughput, available memory, or other suitable limitations), and identify medical applications for which the system cannot presently satisfy respective requirements. Such a system can recommend (e.g., using machine learning) that such applications be hosted independently from the system. Similarly, a system can evaluate compliance with new clinical requirements as applied to existing applications, and determine whether the system can presently meet those requirements, or how the system can be adapted to meet such requirements (e.g., using said machine learning herein).

According to an example, two or more medical applications can share resources. In this example, in response to a medical application of higher priority application requiring system resources currently utilized by a medical application of lower priority, a system herein (e.g., system 102) can rapidly reallocate the sources to the higher priority medical application. According to an embodiment, such priorities herein can correspond to latency requirements. For instance, certain medical applications (e.g., surgical applications) can have a higher priority and stricter latency requirements as compared to a medical image viewing application. Priorities herein can be associated with a type of medical device, clinical procedure, software type, or other suitable identifiers(s) and/or metric(s) for determining priorities of medical applications herein.

In various embodiments, architectures and/or systems described herein can leverage private networks, partially private networks, or other suitable networks, and can additionally or alternatively leverage a common subnet. Further, a single registry instance can run as a service within a Kubernetes cluster. In this regard, Kubernetes can retrieve a container from registry, then run the contents of that container. Further in this regard, a container herein is not directly deployed. A bootstrapper registry can be utilized (e.g., by a system 102) to facilitate operation of systems described herein in addition to other suitable registries. It can be further appreciated that architectures and/or systems described herein enable secure communication (e.g., internal and external communications).

A variety of clustering layers are enabled herein. For instance, a non-cooperative cluster can comprise physical machines which can host Kubernetes cluster virtual machines. A cooperative cluster (e.g., running on a non-cooperative cluster) can comprise a cluster comprising a plurality Kubernetes cluster virtual machines (e.g., worker components herein) regardless of the quantity of physical machines on which the Kubernetes cluster runs atop.

Figure 11:
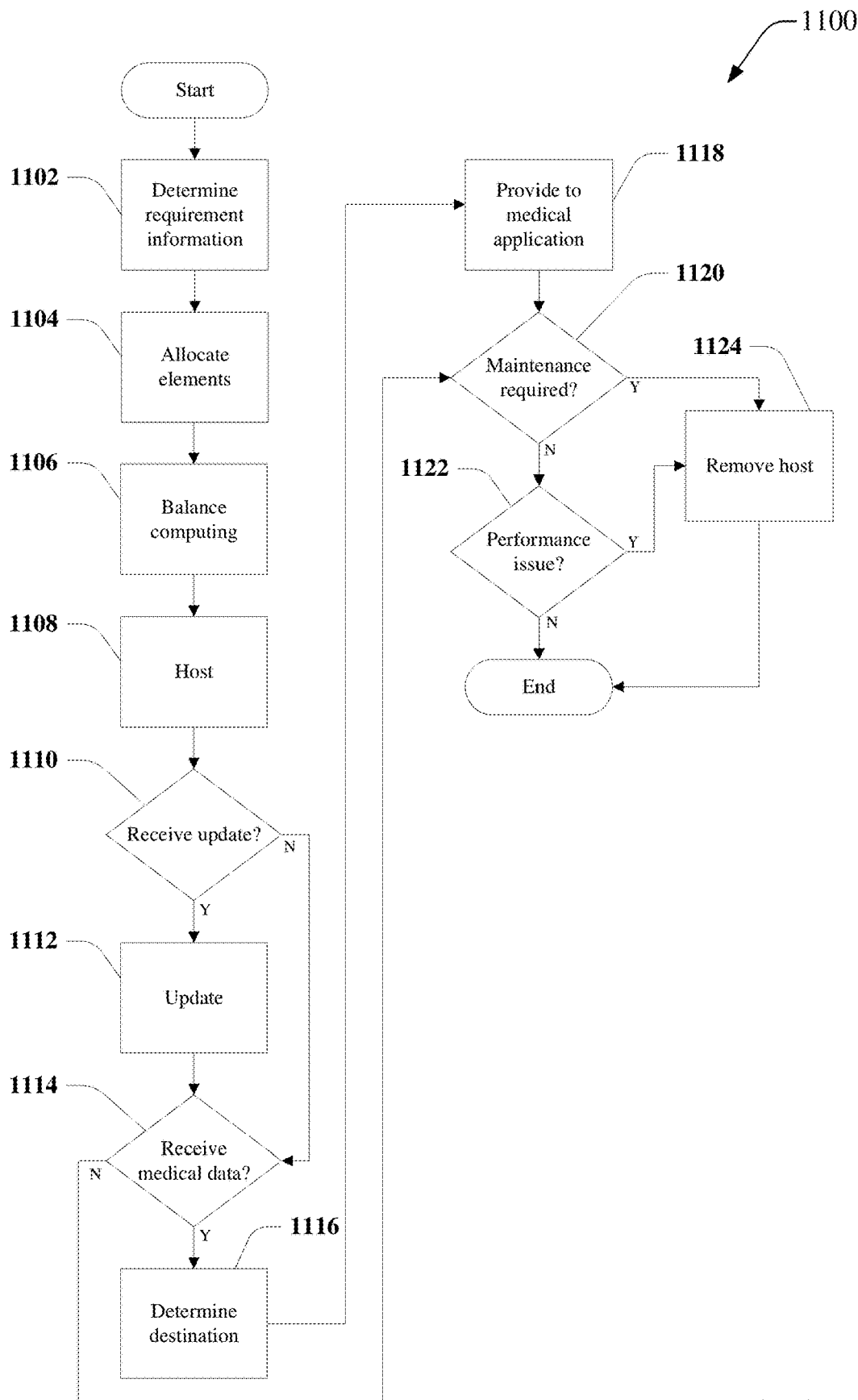
FIG. 11 is a flowchart for a process associated with distributed medical software platforms in accordance with one or more embodiments described herein.

Turning now to FIG. 11, there is illustrated a flow chart of a process 1100 relating to distributed medical software platforms in accordance with one or more embodiments described herein. At 1102, requirement information representative of one or more requirements of an application (e.g., a medical application of a group of medical applications) can be determined (e.g., using a requirement component 110). At 1104, based on the requirement information, elements of a cluster employable to host and run the medical application container can be allocated (e.g., using an allocation component 112). In this regard, the elements of the cluster can be determined to satisfy the requirement information (e.g., by the requirement component 110 or allocation component 112). At 1106, computing can be balanced across hosts in a cluster (e.g., using the balancing component 404). In this regard, each allocated host (e.g., worker component herein) can operate a replica of the medical application in a respective medical application container described herein. At 1108, the medical application can be hosted in respective medical application container(s) (e.g., of one or more worker components described herein). At 1108, if an update (e.g., to a hosted medical application) is received (e.g., via the update component 304), the process can proceed to 1112 at which the update can be applied (e.g., by the update component 304) across the cluster. At 1110, if no update data is received (e.g., by the update component 304), the process can proceed to 1114. At 1114, if medical data is received (e.g., by the control component 108 from a medical device 142) the process can proceed to 1116. If medical data is not received at 1114, the process can proceed to 1120. At 1116, a destination (e.g., destination medical application) can be determined (e.g., using the destination component 204) based on the medical data. At 1118, the medical data can be provided to the determined medical application(s) (e.g., using the destination component 204). At 1120, if maintenance, such as resizing of a system at the compute fabric layer or at the container orchestration cluster layer, applying software patches or updates to the existing installed system or application software, applying a software upgrade to the existing platform software, installing a new application to hosted in the system, installing a new platform application to be available in the system, changing the system configuration, updating a medical application herein, or other suitable maintenance is to be performed on one or more elements (e.g., a host such as worker component herein), the host (e.g., worker component) can be removed (e.g., temporarily) at 1124 from the cluster (e.g. by the removal component 504) so that such maintenance can be performed on the host (e.g., worker component). If at 1120, maintenance is not required, the process can proceed to 1122. If at 1122, a performance issue exists at a host (e.g., host not performing according to defined host specifications), the respective host can be removed (e.g., by the removal component 504) at 1124. If at 1122, no performance issue exists, the process can end (or repeat at 1102).

Figure 12:
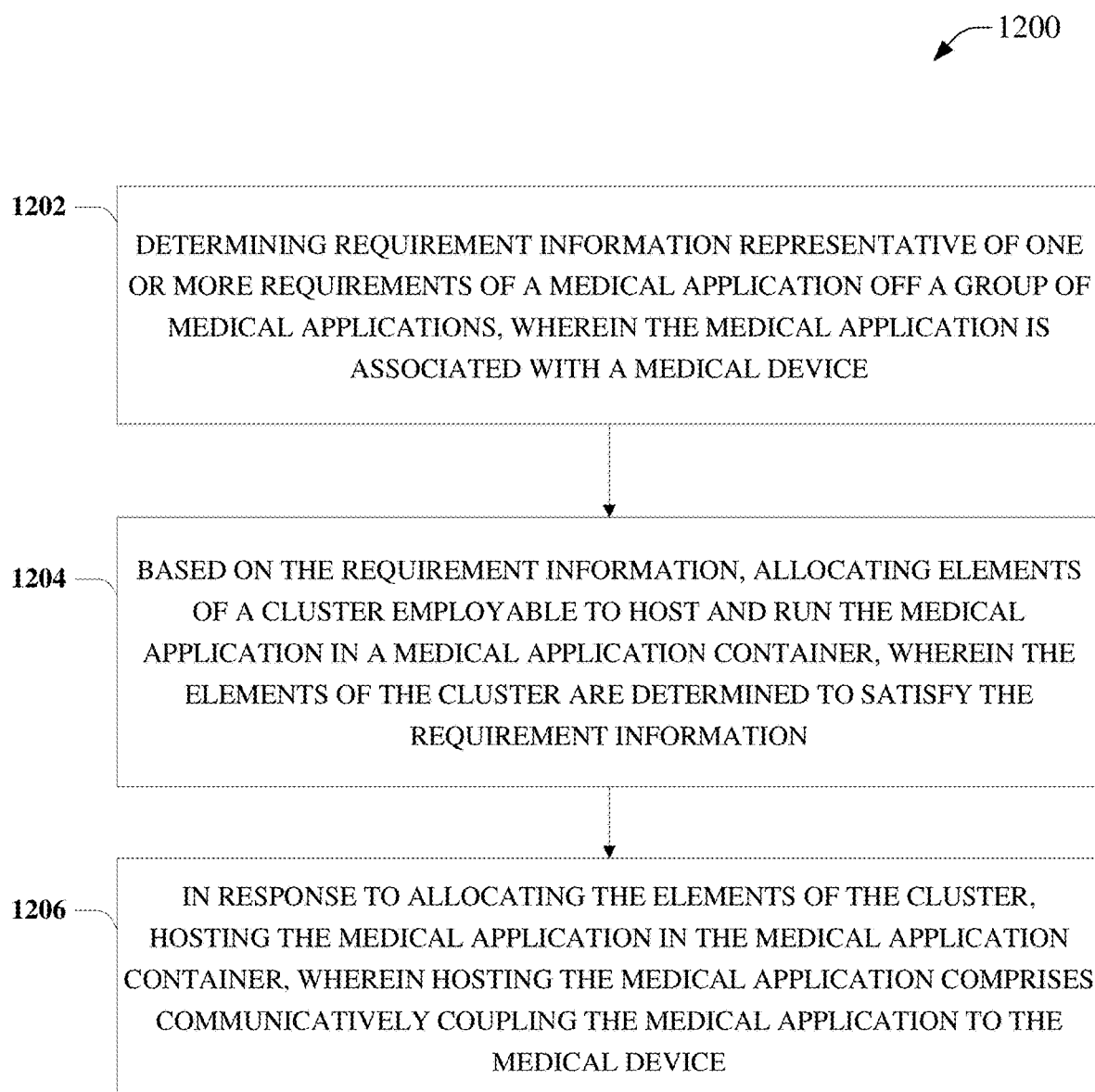
FIG. 12 is a block flow diagram for a process associated with distributed medical software platforms in accordance with one or more embodiments described herein.

FIG. 12 illustrates a block flow diagram for a process 1200 associated with distributed medical software platforms in accordance with one or more embodiments described herein. At 1202, the process 1200 can comprise determining (e.g., using a requirement component 110) requirement information representative of one or more requirements of a medical application (e.g., associated with a medical device) of a group of medical applications. At 1204, the process 1200 can comprise based on the requirement information, allocating (e.g., using the allocation component 112) elements of a cluster employable to host and run the medical application in a medical application container, wherein the elements of the cluster are determined to satisfy the requirement information. At 1206, the process 1200 can comprise in response to allocating the elements of the cluster, hosting (e.g., via a worker component 114 and/or worker component 128) the medical application in the medical application container. It is noted that hosting the medical application can comprise communicatively coupling the medical application to the medical device (e.g., medical device 142).

While, for purposes of simplicity of explanation, the methodologies described herein (e.g., processes 1100, 1200, and additional processes described herein) are shown and described as a series of acts, the disclosed subject matter is not limited by the order of acts, as some acts can occur in different orders and/or concurrently with other acts from that shown and described herein. For example, those skilled in the art will understand and appreciate that a methodology can alternatively be represented as a series of interrelated statuses or events, such as in a state diagram. Moreover, not all illustrated acts may be required to implement a methodology in accordance with the disclosed subject matter. Additionally, it is to be appreciated that the methodologies disclosed in this disclosure are capable of being stored on an article of manufacture to facilitate transporting and transferring such methodologies to computers or other computing devices. Repetitive description of like elements employed in respective examples is omitted for sake of brevity.

Figure 13:
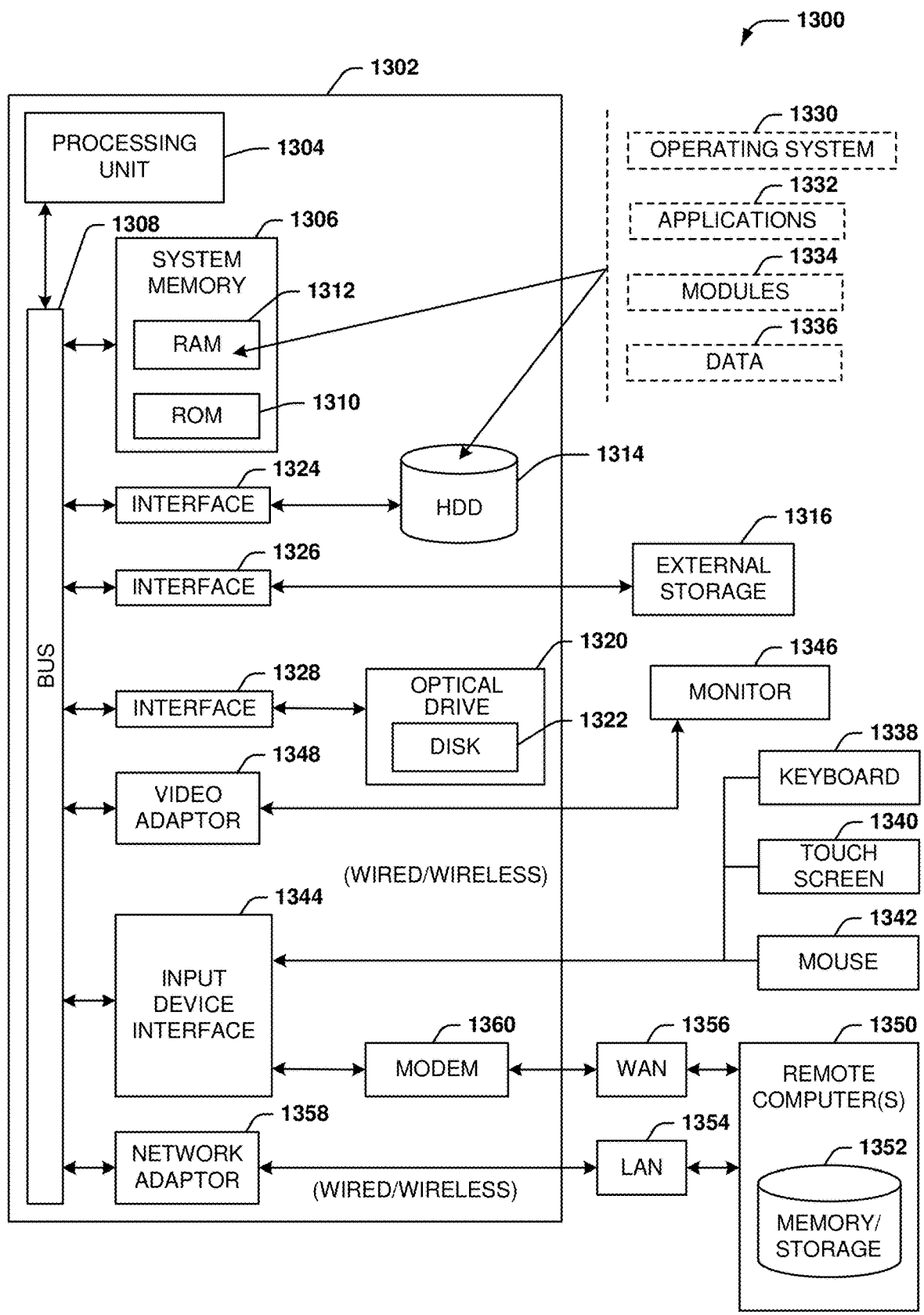
FIG. 13 is an example, non-limiting computing environment in which one or more embodiments described herein can be implemented.

In order to provide additional context for various embodiments described herein, FIG. 13 and the following discussion are intended to provide a brief, general description of a suitable computing environment 1300 in which the various embodiments of the embodiment described herein can be implemented. While the embodiments have been described above in the general context of computer-executable instructions that can run on one or more computers, those skilled in the art will recognize that the embodiments can be also implemented in combination with other program modules and/or as a combination of hardware and software.

Generally, program modules include routines, programs, components, data structures, etc., that perform particular tasks or implement particular abstract data types. Moreover, those skilled in the art will appreciate that the various methods can be practiced with other computer system configurations, including single-processor or multiprocessor computer systems, minicomputers, mainframe computers, Internet of Things (IoT) devices, distributed computing systems, as well as personal computers, hand-held computing devices, microprocessor-based or programmable consumer electronics, and the like, each of which can be operatively coupled to one or more associated devices.

The illustrated embodiments of the embodiments herein can be also practiced in distributed computing environments where certain tasks are performed by remote processing devices that are linked through a communications network. In a distributed computing environment, program modules can be located in both local and remote memory storage devices.

Computing devices typically include a variety of media, which can include computer-readable storage media, machine-readable storage media, and/or communications media, which two terms are used herein differently from one another as follows. Computer-readable storage media or machine-readable storage media can be any available storage media that can be accessed by the computer and includes both volatile and nonvolatile media, removable and non-removable media. By way of example, and not limitation, computer-readable storage media or machine-readable storage media can be implemented in connection with any method or technology for storage of information such as computer-readable or machine-readable instructions, program modules, structured data or unstructured data.

Computer-readable storage media can include, but are not limited to, random access memory (RAM), read only memory (ROM), electrically erasable programmable read only memory (EEPROM), flash memory or other memory technology, compact disk read only memory (CD-ROM), digital versatile disk (DVD), Blu-ray disc (BD) or other optical disk storage, magnetic cassettes, magnetic tape, magnetic disk storage or other magnetic storage devices, solid state drives or other solid state storage devices, or other tangible and/or non-transitory media which can be used to store desired information. In this regard, the terms "tangible" or "non-transitory" herein as applied to storage, memory, or computer-readable media, are to be understood to exclude only propagating transitory signals per se as modifiers and do not relinquish rights to all standard storage, memory or computer-readable media that are not only propagating transitory signals per se.

Computer-readable storage media can be accessed by one or more local or remote computing devices, e.g., via access requests, queries, or other data retrieval protocols, for a variety of operations with respect to the information stored by the medium.

Communications media typically embody computer-readable instructions, data structures, program modules or other structured or unstructured data in a data signal such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared, and other wireless media.

With reference again to FIG. 13, the example environment 1300 for implementing various embodiments of the aspects described herein includes a computer 1302, the computer 1302 including a processing unit 1304, a system memory 1306 and a system bus 1308. The system bus 1308 couples system components including, but not limited to, the system memory 1306 to the processing unit 1304. The processing unit 1304 can be any of various commercially available processors. Dual microprocessors and other multi-processor architectures can also be employed as the processing unit 1304.

The system bus 1308 can be any of several types of bus structure that can further interconnect to a memory bus (with or without a memory controller), a peripheral bus, and a local bus using any of a variety of commercially available bus architectures. The system memory 1306 includes ROM 1310 and RAM 1312. A basic input/output system (BIOS) can be stored in a nonvolatile memory such as ROM, erasable programmable read only memory (EPROM), EEPROM, which BIOS contains the basic routines that help to transfer information between elements within the computer 1302, such as during startup. The RAM 1312 can also include a high-speed RAM such as static RAM for caching data.

The computer 1302 further includes an internal hard disk drive (HDD) 1314 (e.g., EIDE, SATA), one or more external storage devices 1316 (e.g., a magnetic floppy disk drive (FDD) 1316, a memory stick or flash drive reader, a memory card reader, etc.) and an optical disk drive 1320 (e.g., which can read or write from a CD-ROM disc, a DVD, a BD, etc.). While the internal HDD 1314 is illustrated as located within the computer 1302, the internal HDD 1314 can also be configured for external use in a suitable chassis (not shown). Additionally, while not shown in environment 1300, a solid-state drive (SSD) could be used in addition to, or in place of, an HDD 1314. The HDD 1314, external storage device(s) 1316 and optical disk drive 1320 can be connected to the system bus 1308 by an HDD interface 1324, an external storage interface 1326 and an optical drive interface 1328, respectively. The interface 1324 for external drive implementations can include at least one or both of Universal Serial Bus (USB) and Institute of Electrical and Electronics Engineers (IEEE) 1394 interface technologies. Other external drive connection technologies are within contemplation of the embodiments described herein.

The drives and their associated computer-readable storage media provide nonvolatile storage of data, data structures, computer-executable instructions, and so forth. For the computer 1302, the drives and storage media accommodate the storage of any data in a suitable digital format. Although the description of computer-readable storage media above refers to respective types of storage devices, it should be appreciated by those skilled in the art that other types of storage media which are readable by a computer, whether presently existing or developed in the future, could also be used in the example operating environment, and further, that any such storage media can contain computer-executable instructions for performing the methods described herein.

A number of program modules can be stored in the drives and RAM 1312, including an operating system 1330, one or more application programs 1332, other program modules 1334 and program data 1336. All or portions of the operating system, applications, modules, and/or data can also be cached in the RAM 1312. The systems and methods described herein can be implemented utilizing various commercially available operating systems or combinations of operating systems.

Computer 1302 can optionally comprise emulation technologies. For example, a hypervisor (not shown) or other intermediary can emulate a hardware environment for operating system 1330, and the emulated hardware can optionally be different from the hardware illustrated in FIG. 13. In such an embodiment, operating system 1330 can comprise one virtual machine (VM) of multiple VMs hosted at computer 1302. Furthermore, operating system 1330 can provide runtime environments, such as the Java runtime environment or the .NET framework, for applications 1332. Runtime environments are consistent execution environments that allow applications 1332 to run on any operating system that includes the runtime environment. Similarly, operating system 1330 can support containers, and applications 1332 can be in the form of containers, which are lightweight, standalone, executable packages of software that include, e.g., code, runtime, system tools, system libraries and settings for an application.

Further, computer 1302 can be enable with a security module, such as a trusted processing module (TPM). For instance, with a TPM, boot components hash next in time boot components, and wait for a match of results to secured values, before loading a next boot component. This process can take place at any layer in the code execution stack of computer 1302, e.g., applied at the application execution level or at the operating system (OS) kernel level, thereby enabling security at any level of code execution.

A user can enter commands and information into the computer 1302 through one or more wired/wireless input devices, e.g., a keyboard 1338, a touch screen 1340, and a pointing device, such as a mouse 1342. Other input devices (not shown) can include a microphone, an infrared (IR) remote control, a radio frequency (RF) remote control, or other remote control, a joystick, a virtual reality controller and/or virtual reality headset, a game pad, a stylus pen, an image input device, e.g., camera(s), a gesture sensor input device, a vision movement sensor input device, an emotion or facial detection device, a biometric input device, e.g., fingerprint or iris scanner, or the like. These and other input devices are often connected to the processing unit 1304 through an input device interface 1344 that can be coupled to the system bus 1308, but can be connected by other interfaces, such as a parallel port, an IEEE 1394 serial port, a game port, a USB port, an IR interface, a BLUETOOTH® interface, etc.

A monitor 1346 or other type of display device can be also connected to the system bus 1308 via an interface, such as a video adapter 1348. In addition to the monitor 1346, a computer typically includes other peripheral output devices (not shown), such as speakers, printers, etc.

The computer 1302 can operate in a networked environment using logical connections via wired and/or wireless communications to one or more remote computers, such as a remote computer(s) 1350. The remote computer(s) 1350 can be a workstation, a server computer, a router, a personal computer, portable computer, microprocessor-based entertainment appliance, a peer device or other common network node, and typically includes many or all of the elements described relative to the computer 1302, although, for purposes of brevity, only a memory/storage device 1352 is illustrated. The logical connections depicted include wired/wireless connectivity to a local area network (LAN) 1354 and/or larger networks, e.g., a wide area network (WAN) 1356. Such LAN and WAN networking environments are commonplace in offices and companies, and facilitate enterprise-wide computer networks, such as intranets, all of which can connect to a global communications network, e.g., the Internet.

When used in a LAN networking environment, the computer 1302 can be connected to the local network 1354 through a wired and/or wireless communication network interface or adapter 1358. The adapter 1358 can facilitate wired or wireless communication to the LAN 1354, which can also include a wireless access point (AP) disposed thereon for communicating with the adapter 1358 in a wireless mode.

When used in a WAN networking environment, the computer 1302 can include a modem 1360 or can be connected to a communications server on the WAN 1356 via other means for establishing communications over the WAN 1356, such as by way of the Internet. The modem 1360, which can be internal or external and a wired or wireless device, can be connected to the system bus 1308 via the input device interface 1344. In a networked environment, program modules depicted relative to the computer 1302 or portions thereof, can be stored in the remote memory/storage device 1352. It will be appreciated that the network connections shown are example and other means of establishing a communications link between the computers can be used.

When used in either a LAN or WAN networking environment, the computer 1302 can access cloud storage systems or other network-based storage systems in addition to, or in place of, external storage devices 1316 as described above. Generally, a connection between the computer 1302 and a cloud storage system can be established over a LAN 1354 or WAN 1356 e.g., by the adapter 1358 or modem 1360, respectively. Upon connecting the computer 1302 to an associated cloud storage system, the external storage interface 1326 can, with the aid of the adapter 1358 and/or modem 1360, manage storage provided by the cloud storage system as it would other types of external storage. For instance, the external storage interface 1326 can be configured to provide access to cloud storage sources as if those sources were physically connected to the computer 1302.

The computer 1302 can be operable to communicate with any wireless devices or entities operatively disposed in wireless communication, e.g., a printer, scanner, desktop and/or portable computer, portable data assistant, communications satellite, any piece of equipment or location associated with a wirelessly detectable tag (e.g., a kiosk, news stand, store shelf, etc.), and telephone. This can include Wireless Fidelity (Wi-Fi) and BLUETOOTH® wireless technologies. Thus, the communication can be a predefined structure as with a conventional network or simply an ad hoc communication between at least two devices.

Figure 14:
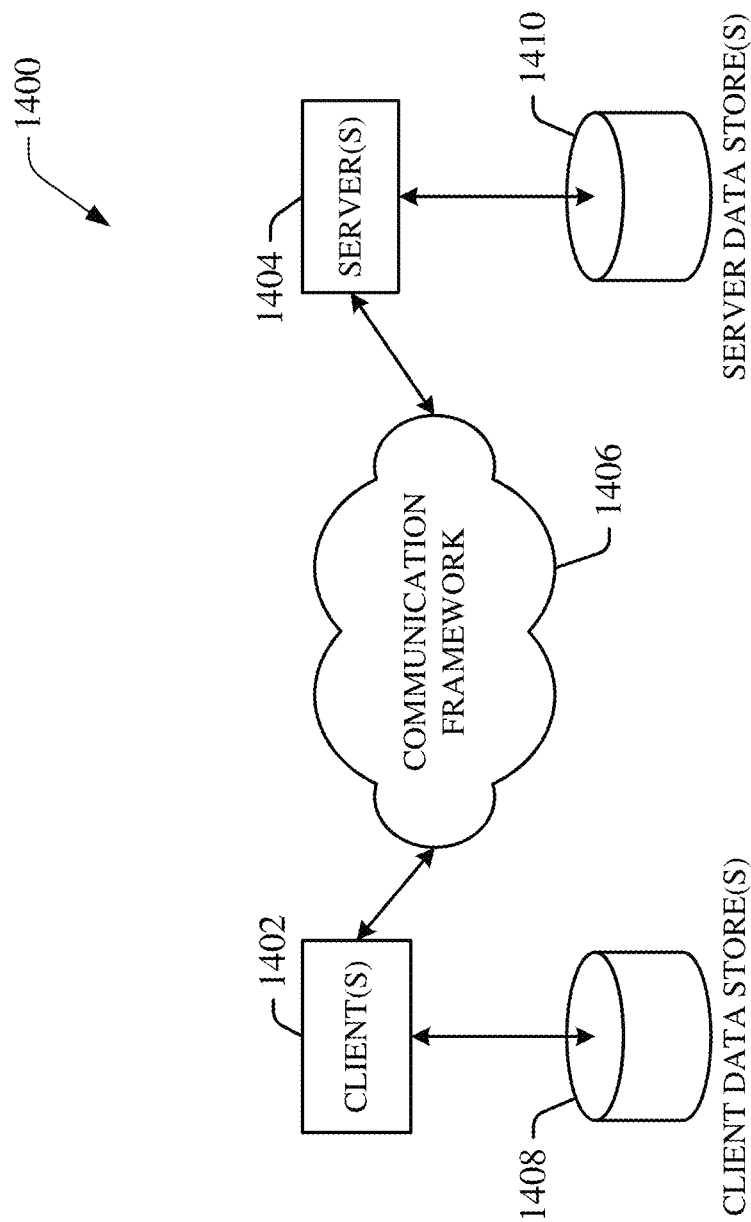
FIG. 14 is an example, non-limiting networking environment in which one or more embodiments described herein can be implemented.

Referring now to FIG. 14, there is illustrated a schematic block diagram of a computing environment 1400 in accordance with this specification. The system 1400 includes one or more client(s) 1402, (e.g., computers, smart phones, tablets, cameras, PDA's). The client(s) 1402 can be hardware and/or software (e.g., threads, processes, computing devices). The client(s) 1402 can house cookie(s) and/or associated contextual information by employing the specification, for example.

The system 1400 also includes one or more server(s) 1404. The server(s) 1404 can also be hardware or hardware in combination with software (e.g., threads, processes, computing devices). The servers 1404 can house threads to perform transformations of media items by employing aspects of this disclosure, for example. One possible communication between a client 1402 and a server 1404 can be in the form of a data packet adapted to be transmitted between two or more computer processes wherein data packets may include coded analyzed headspaces and/or input. The data packet can include a cookie and/or associated contextual information, for example. The system 1400 includes a communication framework 1406 (e.g., a global communication network such as the Internet) that can be employed to facilitate communications between the client(s) 1402 and the server(s) 1404.

Communications can be facilitated via a wired (including optical fiber) and/or wireless technology. The client(s) 1402 are operatively connected to one or more client data store(s) 1408 that can be employed to store information local to the client(s) 1402 (e.g., cookie(s) and/or associated contextual information). Similarly, the server(s) 1404 are operatively connected to one or more server data store(s) 1410 that can be employed to store information local to the servers 1404.

In one exemplary implementation, a client 1402 can transfer an encoded file, (e.g., encoded media item), to server 1404. Server 1404 can store the file, decode the file, or transmit the file to another client 1402. It is noted that a client 1402 can also transfer uncompressed file to a server 1404 and server 1404 can compress the file and/or transform the file in accordance with this disclosure. Likewise, server 1404 can encode information and transmit the information via communication framework 1406 to one or more clients 1402.

The illustrated aspects of the disclosure may also be practiced in distributed computing environments where certain tasks are performed by remote processing devices that are linked through a communications network. In a distributed computing environment, program modules can be located in both local and remote memory storage devices.

The above description includes non-limiting examples of the various embodiments. It is, of course, not possible to describe every conceivable combination of components or methods for purposes of describing the disclosed subject matter, and one skilled in the art may recognize that further combinations and permutations of the various embodiments are possible. The disclosed subject matter is intended to embrace all such alterations, modifications, and variations that fall within the spirit and scope of the appended claims.

With regard to the various functions performed by the above-described components, devices, circuits, systems, etc., the terms (including a reference to a "means") used to describe such components are intended to also include, unless otherwise indicated, any structure(s) which performs the specified function of the described component (e.g., a functional equivalent), even if not structurally equivalent to the disclosed structure. In addition, while a particular feature of the disclosed subject matter may have been disclosed with respect to only one of several implementations, such feature may be combined with one or more other features of the other implementations as may be desired and advantageous for any given or particular application.

The terms "exemplary" and/or "demonstrative" as used herein are intended to mean serving as an example, instance, or illustration. For the avoidance of doubt, the subject matter disclosed herein is not limited by such examples. In addition, any aspect or design described herein as "exemplary" and/or "demonstrative" is not necessarily to be construed as preferred or advantageous over other aspects or designs, nor is it meant to preclude equivalent structures and techniques known to one skilled in the art. Furthermore, to the extent that the terms "includes," "has," "contains," and other similar words are used in either the detailed description or the claims, such terms are intended to be inclusive—in a manner similar to the term "comprising" as an open transition word—without precluding any additional or other elements.

The term "or" as used herein is intended to mean an inclusive "or" rather than an exclusive "or." For example, the phrase "A or B" is intended to include instances of A, B, and both A and B. Additionally, the articles "a" and "an" as used in this application and the appended claims should generally be construed to mean "one or more" unless either otherwise specified or clear from the context to be directed to a singular form.

The term "set" as employed herein excludes the empty set, i.e., the set with no elements therein. Thus, a "set" in the subject disclosure includes one or more elements or entities. Likewise, the term "group" as utilized herein refers to a collection of one or more entities.

The description of illustrated embodiments of the subject disclosure as provided herein, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as one skilled in the art can recognize. In this regard, while the subject matter has been described herein in connection with various embodiments and corresponding drawings, where applicable, it is to be understood that other similar embodiments can be used or modifications and additions can be made to the described embodiments for performing the same, similar, alternative, or substitute function of the disclosed subject matter without deviating therefrom. Therefore, the disclosed subject matter should not be limited to any single embodiment described herein, but rather should be construed in breadth and scope in accordance with the appended claims below.

What is claimed is:

1. A system, comprising:
   a processor; and
   a memory that stores executable instructions that, when executed by the processor, facilitate performance of operations, comprising:
   determining requirement information representative of one or more requirements of a medical application of a group of medical applications, wherein the medical application is associated with a medical device;
   based on the requirement information, allocating elements of a cluster employable to host and run the medical application, wherein the elements of the cluster are determined to satisfy the requirement information, wherein the elements comprise two or more hosts, and wherein each host of the two or more hosts operates a replica of the medical application in respective medical application containers;
   in response to allocating the elements of the cluster, hosting the replica of the medical application in the respective application containers, wherein hosting the replica of the medical application comprises communicatively coupling the replica of the medical application to the medical device; and
   in response to receiving update data representative of an update to the medical application, applying the update data across the replica of the medical application in the respective medical application containers.

2. The system of claim 1, wherein the two or more hosts comprise at least one extra host to host and run the medical application in a medical application container in addition to a minimum quantity of hosts determined, based on the requirement information, to be required to host and run the medical application in the medical application container.

3. The system of claim 1, wherein the operations further comprise:

in response to receiving medical data from the medical device, determining, based on the medical data, a destination application for the medical data, wherein the destination application is determined to be the medical application.

4. The system of claim 1, wherein the cluster is distributed across a first server located at a customer site and a second server located at a cloud storage site, and wherein the customer site is different from the cloud storage site.

5. The system of claim 1, wherein the applying the update comprises:
removing individual containers of the respective medical application containers one at a time to update the replica of the medical application such that a minimum quantity of compute capability to host and run the medical application is maintained.

6. The system of claim 1, wherein the medical device comprises an international electrotechnical commission 62304 Class C medical device.

7. The system of claim 1, wherein the cluster comprises a containerized machine learning service employable by the medical application to facilitate machine learning operations associated with the medical application.

8. The system of claim 1, wherein the cluster comprises a containerized digital imaging and communications in medicine service employable by the medical application to facilitate medical imaging operations associated with the medical application.

9. The system of claim 1, wherein the medical application comprises a verified and validated medical application according to a clinical regularity requirement.

10. The system of claim 1, wherein the operations further comprise:
balancing computing associated with the medical application across the two or more hosts.

11. A non-transitory machine-readable medium, comprising executable instructions that, when executed by a processor, facilitate performance of operations, comprising:
based on the requirement information, allocating elements of a cluster employable to host and run the medical application, wherein the elements of the cluster are determined to satisfy the requirement information, wherein the elements comprise two or more hosts, and wherein each host of the two or more hosts operates a replica of the medical application in respective medical application containers;
in response to allocating the elements of the cluster, hosting the replica of the medical application in the respective application containers, wherein hosting the replica of the medical application comprises communicatively coupling the medical application to the medical device; and
in response to receiving update data representative of an update to the medical application, applying the update data across the replica of the medical application in the respective medical application containers.

12. The non-transitory machine-readable medium of claim 11, wherein the operations further comprise:
balancing computing associated with the replica of the medical application across the two or more hosts.

13. The non-transitory machine-readable medium of claim 12, wherein the two or more hosts comprise at least one extra host to host and run the medical application in a medical application container in addition to a minimum quantity of hosts determined, based on the requirement information, to be required to host and run the medical application in the medical application container.

14. The non-transitory machine-readable medium of claim 12, wherein the two or more hosts comprise two or more virtual machines, and wherein the operations further comprise:
generating, using a hypervisor, the two or more virtual machines based on the requirement information.

15. The non-transitory machine-readable medium of claim 11, wherein the operations further comprise:
in response to receiving medical data from the medical device, determining, based on the medical data, destination applications for the medical data from among the group of medical applications, wherein the destination applications comprise the medical application.

16. A method, comprising:
determining, by distributed medical software platform hosting equipment comprising a processor, requirement information representative of one or more requirements of a medical application of a group of medical applications, wherein the medical application is associated with a medical device;
based on the requirement information, allocating, by the distributed medical software platform hosting equipment, elements of a cluster employable to host and run the medical application, wherein the elements of the cluster are determined to satisfy the requirement information, wherein the elements comprise two or more hosts, and wherein each host of the two or more hosts operates a replica of the medical application in respective medical application containers;
in response to allocating the elements of the cluster, hosting, by the distributed medical software platform hosting equipment, the replica of the medical application in the respective application containers, wherein hosting the medical application comprises communicatively coupling the replica of the medical application to the medical device; and
in response to receiving update data representative of an update to the medical application, applying, by the distributed medical software platform hosting equipment, the update data across the replica of the medical application in the respective medical application containers.

17. The method of claim 16, wherein the two or more hosts comprise at least one extra host to host and run the medical application in a medical application container in addition to a minimum quantity of hosts determined, based on the requirement information, to be required to host and run the medical application in the medical application container.

18. The method of claim 17, further comprising:
removing, from the two or more hosts, by the distributed medical software platform hosting equipment, a host in response to a host removal criterion being determined to be satisfied.

19. The method of claim 18, wherein the host removal criterion comprises a maintenance criterion.

20. The method of claim 18, wherein the host removal criterion comprises a performance criterion.

* * * * *